United States Patent
Mundt et al.

(10) Patent No.: US 9,670,456 B2
(45) Date of Patent: Jun. 6, 2017

(54) VIRUS FILTRATION OF CELL CULTURE MEDIA

(71) Applicants: BAXALTA GMBH, Opfikon (CH); BAXALTA INCORPORATED, Bannockburn, IL (US)

(72) Inventors: Wolfgang Mundt, Vienna (AT); Artur Mitterer, Orth/Donau (AT); Manfred Reiter, Vienna (AT); Meinhard Hasslacher, Vienna (AT); Leopold Grillberger, Vienna (AT); Thomas Kreil, Klosterneuburg (AT)

(73) Assignees: BAXALTA GMBH, Opfikon (CH); BAXALTA INCORPORATED, Bannockburn, IL (US)

( * ) Notice: Subject to any disclaimer, the term of this patent is extended or adjusted under 35 U.S.C. 154(b) by 225 days.

(21) Appl. No.: 13/921,417

(22) Filed: Jun. 19, 2013

(65) Prior Publication Data

US 2013/0344535 A1    Dec. 26, 2013

Related U.S. Application Data

(60) Provisional application No. 61/662,814, filed on Jun. 21, 2012.

(51) Int. Cl.
| | |
|---|---|
| *C12N 7/02* | (2006.01) |
| *C12N 5/071* | (2010.01) |
| *A61L 2/00* | (2006.01) |
| *C12M 1/00* | (2006.01) |
| *C12M 1/12* | (2006.01) |

(52) U.S. Cl.
CPC .......... *C12N 5/0602* (2013.01); *A61L 2/0017* (2013.01); *C12M 29/26* (2013.01); *C12M 37/02* (2013.01)

(58) Field of Classification Search
None
See application file for complete search history.

(56) References Cited

U.S. PATENT DOCUMENTS

| | | | |
|---|---|---|---|
| 6,485,686 B1 * | 11/2002 | Wick | G01N 1/2273 |
| | | | 422/504 |
| 7,144,533 B2 | 12/2006 | Koslow | |
| 8,309,029 B1 * | 11/2012 | Wick | G01N 1/2202 |
| | | | 422/50 |
| 2008/0213753 A1 * | 9/2008 | Henning | C12N 7/00 |
| | | | 435/5 |

FOREIGN PATENT DOCUMENTS

| | | |
|---|---|---|
| EP | 1 457 497 | 9/2004 |
| EP | 1 775 016 | 4/2007 |

OTHER PUBLICATIONS

Baxter International, Inc., "Notification of Transmittal of the International Search Report and the Written Opinion of the International Searching Authority, or the Declaration," for PCT/US2013/045663, dated Sep. 5, 2013, 10 pages.

Liu et al., "Development and Quantification of a Novel Virus Removal Filter for Cell Culture Applications," Biotechnol. Prog., vol. 16, pp. 425-434, Mar. 5, 2000.

Jessika Allard (2004) "The effect of viral clearance methods on protein quality" Molecular Biotechnology Programme, Uppsala University School of Engineering, ISSN 1401-2138, 44 pages.

http://www.lenntech.com/Data-sheets/Viresolve-NFP-Filter-Cartridges-L.pdf.

* cited by examiner

*Primary Examiner* — Blaine Lankford
(74) *Attorney, Agent, or Firm* — Troutman Sanders LLP

(57) ABSTRACT

The invention relates to a method for removing a viral contaminant from a preparation, being a cell culture medium or at least a component of a cell culture medium. The method comprises subjecting said preparation to filtration for at least about 24 hours through a virus filter having an effective pore size of maximum about 75 nm. Further, the invention relates to the use of a virus filter in filtration of at least about 24 hours, wherein the virus filter has an effective pore size of maximum about 75 nm for the removal of viral contaminant from a preparation, being a cell culture medium or at least a component of a cell culture medium. In some embodiments the filtration according to the invention operates at a volumetric capacity of at least about 2000 $L/m^2$. Further, the invention relates to the use of a preparation, being a cell culture medium or at least a component of a cell culture medium obtainable according to method of the invention for cell culture; pharmaceutical, diagnostic and/or cosmetic preparations as well as in food preparations.

19 Claims, 11 Drawing Sheets

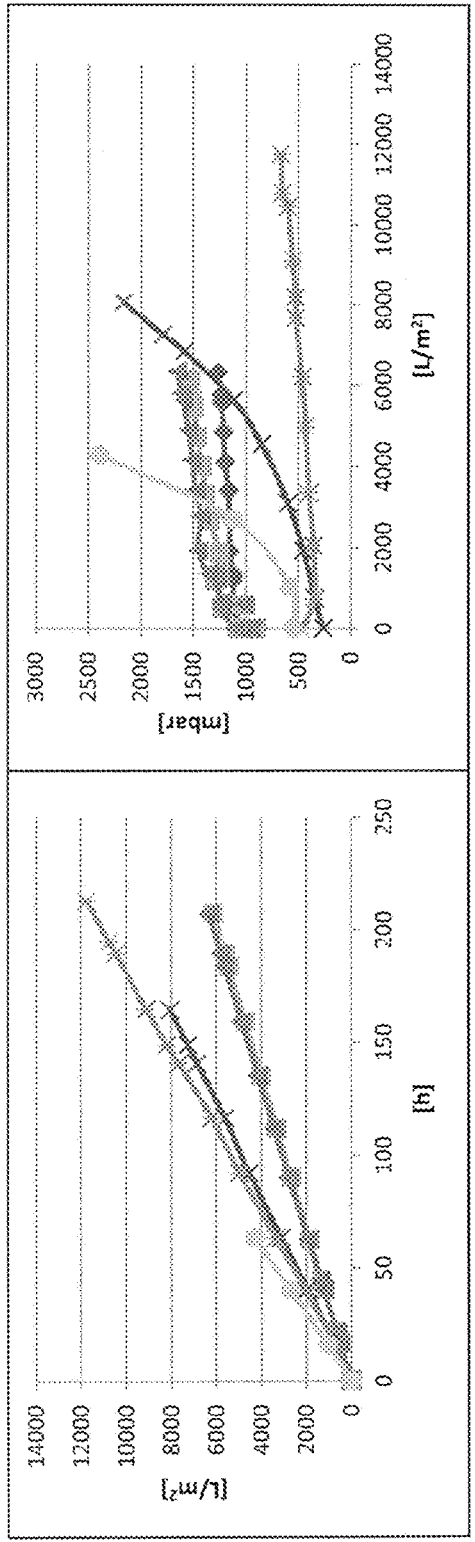
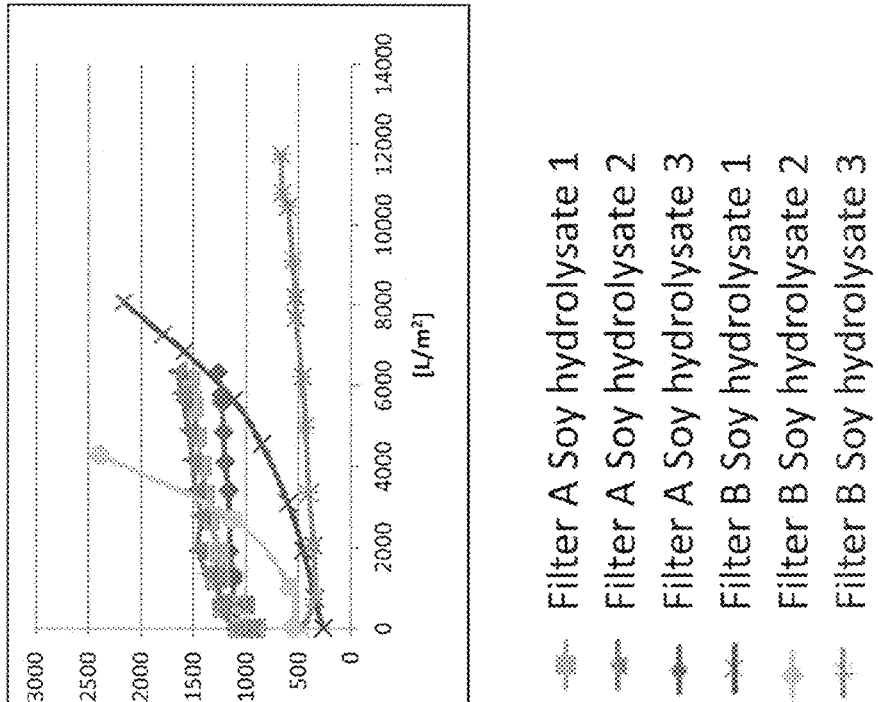
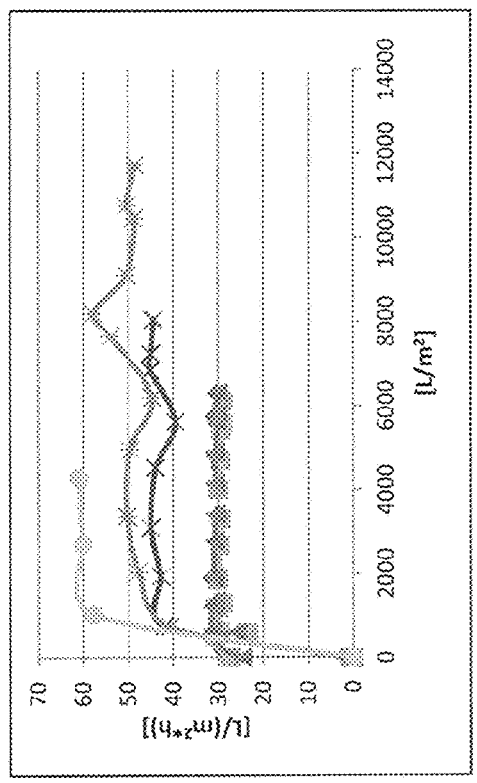
Figure 1A
Figure 1B
Figure 1C
- Filter A Soy hydrolysate 1
- Filter A Soy hydrolysate 2
- Filter A Soy hydrolysate 3
- Filter B Soy hydrolysate 1
- Filter B Soy hydrolysate 2
- Filter B Soy hydrolysate 3

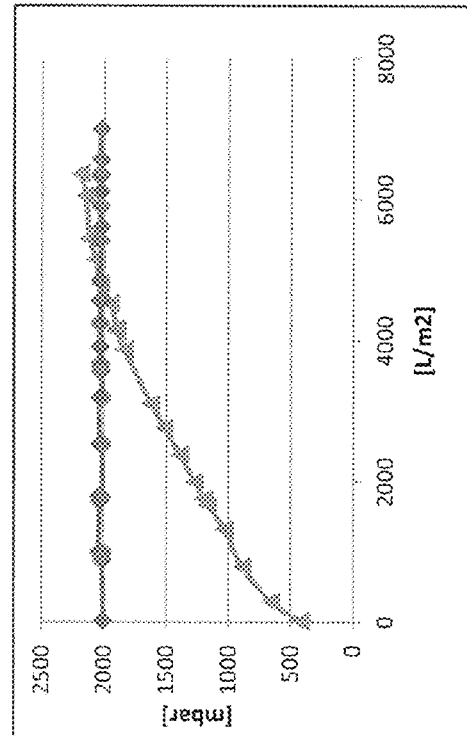
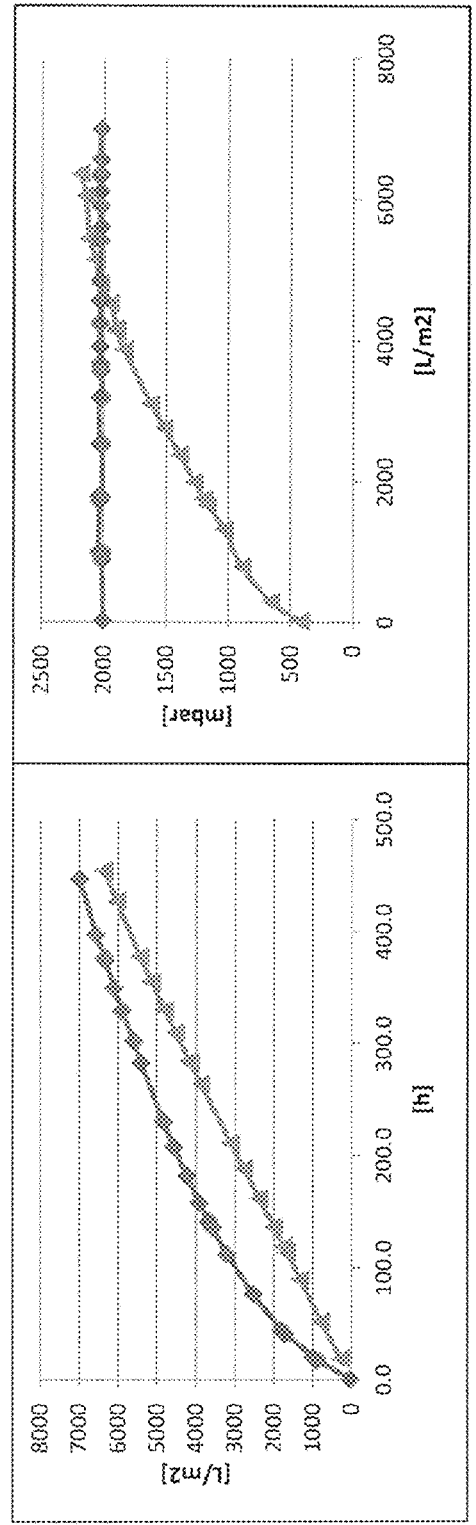
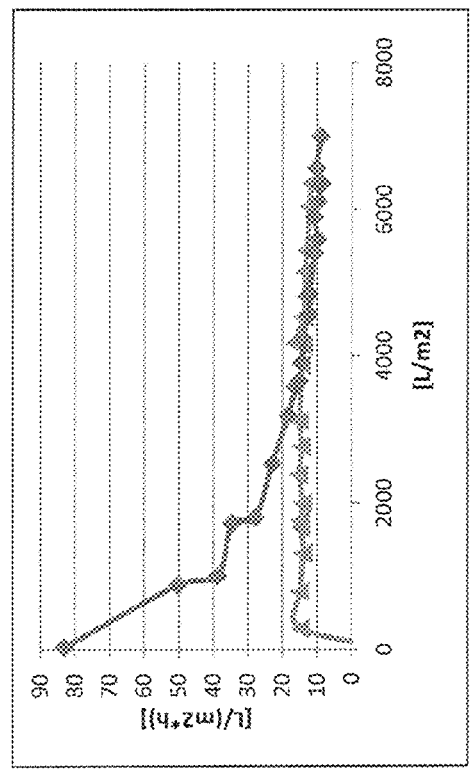
Figure 4A
Figure 4B
Figure 4C

Figure 11

| Spiked Material | Feed Volume [mL] | MMV Titer [log₁₀(TCID₅₀/mL)] 5.0 | MMV Load [log₁₀(TCID₅₀)] 8.5 |
|---|---|---|---|
| NF day 1 | 287 | < -0.8 | < 1.7 |
| NF day 2 | 272 | < -0.8 | < 1.6 |
| NF day 3 | 246 | < -0.8 | < 1.6 |
| NF day 7 | 330 | < 0.3 | < 2.8 |
| NF day 8 | 216 | < -0.8 | < 1.5 |
| NF day 9 | 118 | < -0.8 | < 1.3 |
| NF day 10 | 121 | < -0.8 | < 1.3 |
| NF day 13 | 368 | < -0.8 | < 1.8 |
| NF day 14 | 106 | < -0.8 | < 1.2 |
| NF day 15 | 98 | < -0.8 | < 1.2 |
| NF day 16 | 99 | < -0.8 | < 1.2 |
| NF day 17 | 96 | < -0.8 | < 1.2 |
| NF day 21 | 354 | < -0.8 | < 1.7 |
| NF day 22 | 69 | < -0.8 | < 1.0 |
| NF day 23 | 74 | < -0.8 | < 1.1 |
| NF day 24 | 67 | < -0.8 | < 1.0 |
| NF day 27 | 194 | < -0.8 | < 1.5 |
| NF day 28 | 57 | < -0.8 | < 1.0 |
| NF day 29 | 49 | < -0.8 | < 0.9 |
| NF day 30 | 52 | < -0.8 | < 0.9 |
| Total Filtered Volume | 3,270 | | < 3.0 |
| L/m² | 6,540 | | |
| RF | | | > 5.5 log₁₀ |

VIRUS FILTRATION OF CELL CULTURE MEDIA

BACKGROUND OF THE INVENTION

Virological safety is a significant concern in the biopharmaceutical industry. Despite efforts to mitigate the risk, incidents involving large-scale viral contamination of biologics have raised concern in the industry. Highly profiled events include, for example, Genzyme's 2009 detection of a Vesivirus 2117 contamination of its CHO (Chinese hamster ovary) cell culture which halted production of Cerezyme® and Fabrazyme® and Merck's 2010 contamination of its Rotarix® vaccine by porcine circovirus 1. A likely source of contamination is at the cell culture stage. In addition to the economic toll on the manufacturing company (one report puts the estimate at over hundred million loss per 10000 L bioreactor contamination plus fines from the agencies), such events pose a risk to patients and disrupt access to the biopharmaceutical products (Liu et al., Biotechnol. Prog. 2000, 16, 425-434). As a result, there is heightened regulatory scrutiny and demand for new techniques to detect, prevent, and remediate viral contaminations.

In general, viral contaminants can be differentiated into upstream and downstream viral contaminations. Downstream contaminations may be controlled by applying closed systems, however, especially upstream contaminations are difficult to control and detect even by extensive testing. Viral contaminants may also originate from the use of animal derived materials in the biopharmaceutical production. Where the production cell line is free of extraneous viral contaminants and production does not involve use of animal derived materials, viral contaminants could still enter by way of cell culture media. For instance, synthetic media may be supplemented with recombinant growth factors produced in a serum-supplemented system and protein-free medium may nevertheless contain filtered protein hydrolysates. However, viral contamination may even occur in completely chemically defined medium, because large quantities of medium components may be packed in non-sterile containers. Conventional sterilizing-grade filters are neither designed to nor capable of safeguarding against viral contaminants, so other measures must be employed to ensure virological safety.

Detection of adventitious viruses at one or more checkpoints of the production process is standard practice. However, detection alone is an inadequate measure against viral contamination of biopharmaceutical products, especially where the viral contaminant present is unsuspected, unknown, or an emerging viral agent. Such viral agents can escape detection by even well-designed DNA microarrays representative of a large collection of sequenced viruses. The challenge is further compounded by the low levels of viral contaminants needed to infect a cell culture and currently limited detection assay sensitivity.

High titers of the viral contaminant may not manifest in the form of altered cell culture parameters, e.g. culture density, protein titers, beyond their normal range. On the other hand, infectivity assays are highly specific and require different conditions for each virus. As a result of viral contamination, downstream equipment, fluids, and products can be tainted, incurring millions of dollars in batch setup, waste disposal, lost sales, and decontamination. Thorough screening of raw materials for viruses is difficult due to sample heterogeneity and the large volumes involved in biopharmaceutical production processes.

Viral clearance techniques can be classified into one of two groups: inactivation and filtration. Inactivation methods seek the irreversible loss of viral infectivity, whereas filtration methods seek to mechanically reduce the viral contaminant. Conventional inactivation methods employ ultraviolet (UV) irradiation, gamma irradiation, heat, low or high pH, or solvent/detergent exposure. In instances where UV irradiation can effectively and irreversibly eliminate viral activity, it may be impractical on a large-scale basis or unsuitable for prepared media. Autoclaving, while possible for heat-stable liquids, may alter sensitive media. An alternative method known as high-temperature, short-time (HTST) heat treatment is not as harsh but demands costly equipment, automation, and validation procedures to preserve the media characteristics. Low or high pH exposure is ineffective across the spectrum of possible viral contaminants and can negatively impact the quality or osmolarity of the media. Solvent/detergent exposure is likewise not a broad-spectrum solution and is effective only for viruses with a lipid envelope. As such, the ideal method should balance cost considerations and the needs to effect viral clearance in raw materials and provide a broad-spectrum solution without compromising growth rate or yield.

Viral-retentive filtration offers the appropriate balance. It does not chemically alter media components and is suitable for use with heat-sensitive feed/media. Furthermore, viral-retentive filtration is a broad-spectrum solution since it operates on a size exclusion principle. However, viral-retentive membranes are costly (approximately about 2000 to 5000 EUR per $m^2$). The low specific flow rates characteristic of filtration of media volumes have made the method economically taxing on a scale suitable for large scale bioreactor supply, due to the cost of the membrane area needed. For example, where virus filtration is connected in-series to sterilizing grade media filtration, virus filtration preferably needs to occur within a working day, i.e. a maximum of 2 to 10 hours after preparation of the bulk medium in order to prevent contamination of the bulk medium. Therefore, a large filtration area is needed to stay within this critical time window, which in turn raises costs.

Surprisingly, it has been found that the drawbacks of said prior art virus filtration can be overcome by filtration of the respective preparation, being a cell culture medium or at least a component of a cell culture medium, for at least about 24 hours through a virus filter having an effective pore size of maximum 75 nm. If the required volume of the respective preparations is filtered during a longer time frame, i.e. for at least 24 hours the volumetric capacity of the virus filters increase enormously. Surprisingly, it has been found additionally that significant overall virus titer reduction can be achieved over this extended period of time. This is especially beneficial in upstream virus removal in cell culture systems.

Therefore, the method of the invention enhances the economic efficiency of virus filtration by enhancing throughput and volumetric capacity, respectively. The method according to the present invention operates at a volumetric capacity of at least 2000 $L/m^2$, thereby helping to maximize the use of high capacity virus filters, decreasing the effective costs associated therewith, and presenting a solution practicable on a large scale and readily integrable into existing production processes.

The enormous impact of the method according to the invention and the inventive use of the respective virus filters on sterile manufacturing processes, in particular processes where sterile preparations, e.g. cell culture media and buffers, are used can be understood by means of the following example. Assuming that a square meter of a virus filter membrane costs about 3000 EUR in average and a cell culture medium is used costing about 10 EUR per liter medium, then the costs for 1000 L virus filtered media are 13 EUR per liter medium, which increases the costs of goods for media preparation by about 30%. If 2000 L can be filtered with a virus filter membrane then the costs decrease to 11.50 EUR. Further increase of volumetric capacities, e.g. beyond 5000 L reduces the costs to less than 0.6 EUR per liter medium, which makes the additional costs for providing a virus filtered medium considerably low. As a result, the high costs of using virus filters, in particular in upstream decontamination of potential viral or viral contamination decreases significantly by increasing the volumetric capacity of the virus filtration method.

The present invention fully addresses this problem of high costs and low volumetric capacity of virus filters, respectively. The volumetric capacity of the virus filter can be increased by performing the virus filtration for at least about 24 hours through a virus filter having an effective pore size of maximum 75 nm. Surprisingly, it has been found that the volumetric capacity of the used costly virus filters can be better exploited leading to a 2 to 100-fold increase of the volumetric capacity while maintaining the filter integrity. Although a 2 to 3-fold increase of volumetric capacity already has a great impact to the production process and the related production costs, with the method according to the invention an up to 100-fold increase of volumetric capacity or even more can be achieved. This offers great opportunities and makes viral removal cost efficient even with costly virus filters that now can be used to further improve viral safety in cell culture processes, in particular in upstream viral removal of cell culture processes, pharmaceutical, diagnostic and/or cosmetic and food processes.

SUMMARY OF THE INVENTION

The present invention provides a method for removing a viral contaminant from a preparation, being a cell culture media or at least a component of a cell culture media. The method comprises subjecting said preparation to filtration for at least about 24 hours through a virus filter having an effective pore size of maximum 75 nm.

Further, the invention relates to the use of a virus filter having an effective pore size of maximum 75 nm in a filtration for at least about 24 hours for the removal of viral contaminant from a preparation, being a cell culture media or at least a component of a cell culture media.

In addition, the invention relates to the use of a preparation, being a cell culture media or at least a component of a cell culture media obtainable according to any method of the present invention for cell culture; pharmaceutical, diagnostic and/or cosmetic preparations as well as in food preparations.

All methods and uses according to the invention can operate at a volumetric capacity of at least about 2000 L/m$^2$, preferably at least about 3000 L/m$^2$, most preferably at least about 5000 L/m$^2$. In addition, the preparation is subjected to filtration and the filtration is performed, respectively, for at least 24 hours or for at least about 48 hours up to about 7 months or about 72 hours up to about 3 months. The filtration is performed at a temperature from about 2° C. to about 60° C., or about 10 to about 40° C., preferably about 15 to about 37° C.

In all embodiments of the invention filtration is performed at a pressure ranging from about 100 mbar to about 4000 mbar, preferably from about 200 mbar to about 3500 mbar, most preferably from about 1000 mbar to about 3000 mbar.

In all embodiments of the invention the used virus filter achieves at least a 1 $Log_{10}$ reduction value (LRV) for a viral contaminant.

Surprisingly, it has been found that the volumetric capacity of virus filters can be enormously increased when operating the filtration process for at least about 24 hours. Normally, preparations for cell culture e.g. bulk cell culture media or buffers are filtered batchwise within about 2 to about 10 hours after preparation of the bulk preparations in order to avoid contamination of the preparations by bacterial or viral growth. It has turned out that in practice the maximum capacity of the used virus filters is not nearly exploited in filtration processes filtering the respective preparations within a timeframe of about 2 to about 10 hours. Therefore excessive filter area has to be used. In contrast thereto, it has been found that due to the use of the method of the present invention, the volumetric capacity of the used costly virus filters can be better exploited leading to a 2 to 100-fold increase of the volumetric capacity while maintaining the filter integrity. Although a 2 to 3-fold increase of volumetric capacity already has a great impact to the production process and the related production costs, with the method according to the invention an up to 100-fold increase or even more can be achieved. This offers great opportunities and makes viral removal cost efficient even with costly virus filters that now can be used to further improve viral safety in cell culture processes, in particular in upstream viral removal of cell culture processes, pharmaceutical, diagnostic and/or cosmetic and food processes.

Specific preferred embodiments of the present invention will become evident from the following more detailed description of certain embodiments and the claims.

BRIEF DESCRIPTION OF THE DRAWINGS

More particular descriptions of the invention are made by reference to certain exemplary embodiments thereof which are illustrated in the appended Figures. These Figures form a part of the specification. It is to be noted, however, that the appended Figures illustrate exemplary embodiments of the invention and therefore are not to be considered limiting in their scope.

FIG. 1 is showing the virus filtration kinetics performed applying a flow controlled virus filtration (FIG. 1C) using different filters all combined with cell culture media supplemented with 3 different soy hydrolysate lots (Kerry HyPep1510 #1, DOMO SE50 MAF UF #1 and #2).

Filter and experimental conditions applied (see also Example 1 to Example 4):

Filter A: Sartorius Virosart CPV, 180 cm$^2$; at 30° C. with flow rates of about 30 L/(m$^2$×hr)

Filter B: Millipore Viresolve NFP 3.1 cm$^2$; at 30° C. with flow rates of about 40-60 L/(m$^2$×hr). Filtrations were carried out for up to a maximum of 9 days or until a maximum pressure of 2000 mbar was exceeded. FIG. 1A is showing the volumetric capacity as filtered volume per membrane surface area plotted against the time, ranging from about minimum 4000 L/m$^2$ to about 12000 L/m$^2$. Maximum pressure at the end of filtration was between about 600 mbar and 2400 mbar dependent on the filter type (FIG. 1B). In general the difference between the soy hydrolysates is considerably low for the volumetric capacity and the maximum pressure.

Figure 2A:
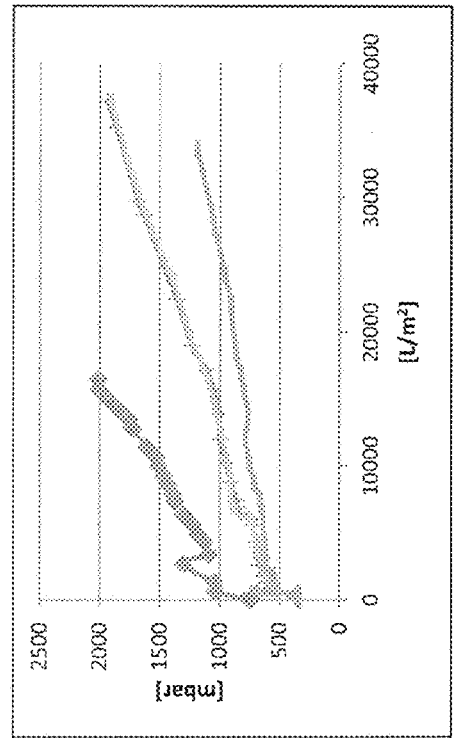
Figure 2B:
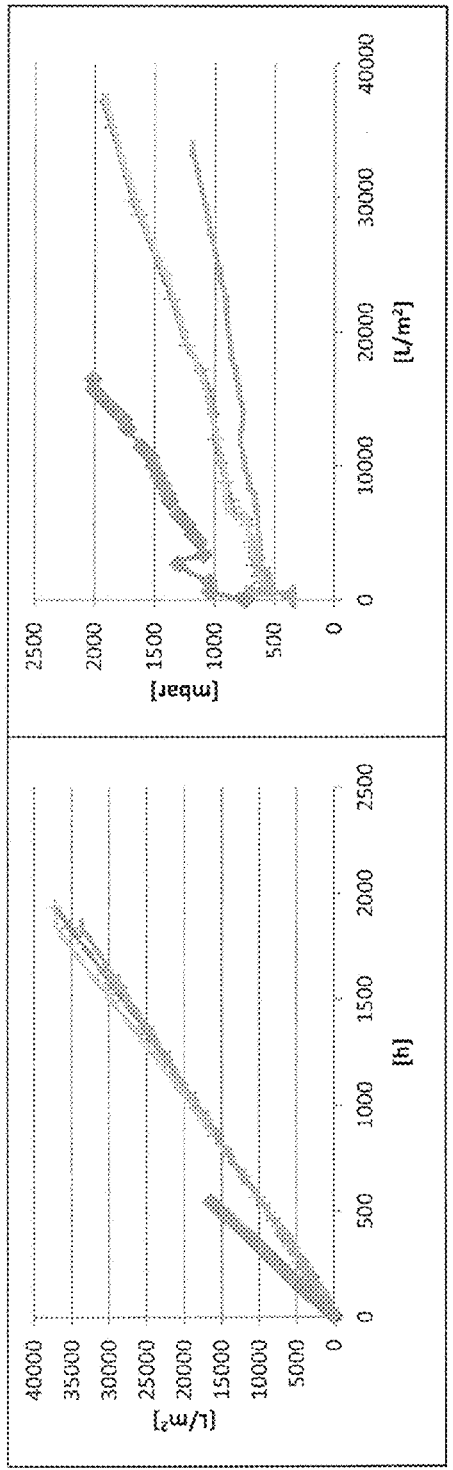
Figure 2C:
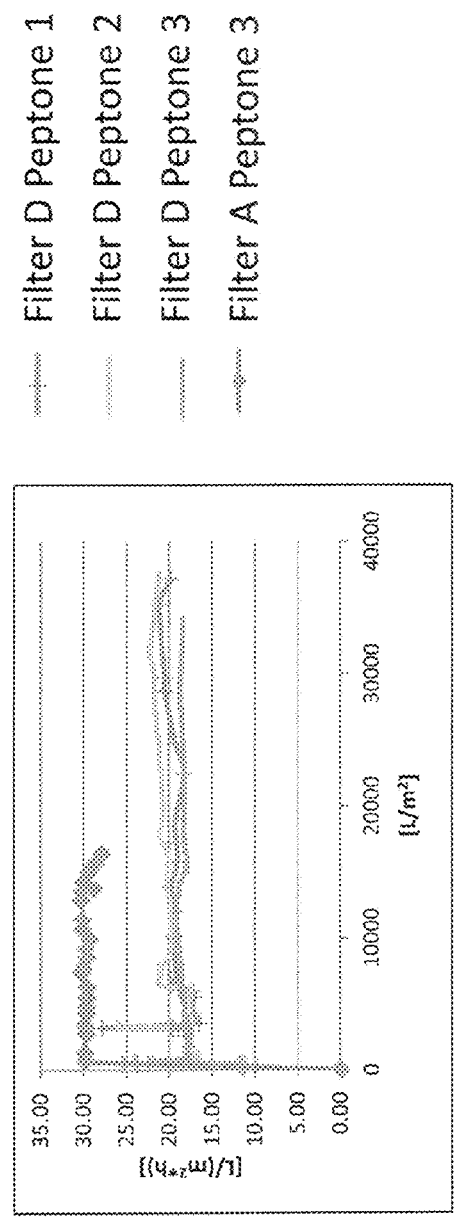

FIG. 2 is showing the virus filtration kinetics performed applying a flow controlled virus filtration (FIG. 2C) using different filters and cell culture media supplemented with 3 different soy hydrolysate lots (Kerry HyPep 1510 #1, DOMO SE50 MAF UF #1 and #2).

Filter and experimental conditions applied (see also Example 1 to Example 4):

Filter A: Sartorius Virosart CPV, 180 cm$^2$; at 30° C. with flow rates of about 30 L/(m$^2$×hr)

Filter D: Asahi BioEX 10 cm$^2$; at ambient temperature (about 22° C.) with flow rates of about 20 L/(m$^2$×hr). In contrast to the experiments described in FIG. 1, the filtrations were carried out for a longer time span up to 81 days or until a pressure of 2000 mbar was reached. FIG. 2A is showing the volumetric capacity as filtered volume per membrane surface area plotted against the time, ranging from about minimum 16000 L/m$^2$ (for filter A with DOMO SE50 MAF #2) to about 35000 L/m$^2$ (for filter D with all 3 different hydrolysate lots). Maximum pressure at the end of filtration was between about 1200 mbar and 2000 mbar dependent on the filter type (FIG. 2B). In general the difference between the soy hydrolysates is considerably low for the volumetric capacity and the maximum pressure.

Figure 3:
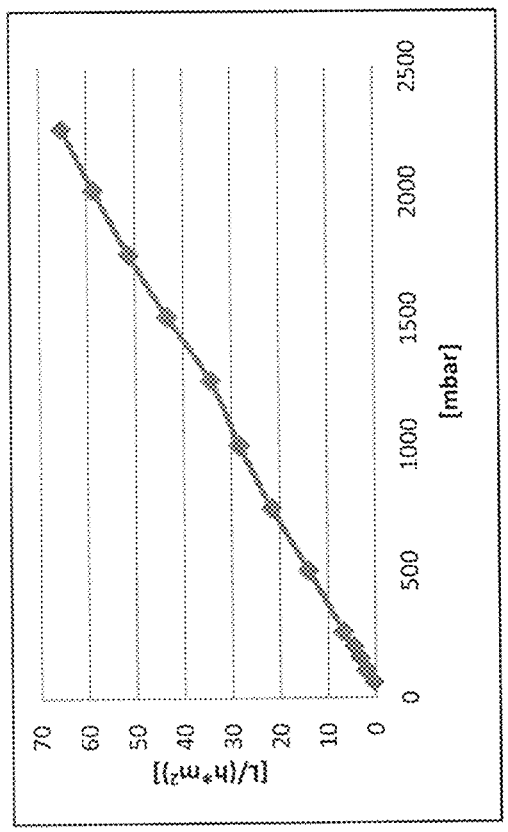

FIG. 3 is a graph showing the relationship between flux and differential pressure as observed at about 22° C. using Filter A (Sartorius Virosart CPV 180 cm$^2$) and media containing soy hydrolysate DOMO SE50 MAF UF, Lot #2 (see Example 5).

A minimum differential pressure of about 100 mbar is required to achieve a minimum detectable specific flow rate, which is then gradually increasing with an obviously linear proportional correlation between specific flow rate and differential pressure.

FIG. 4 is showing the difference between a pressure controlled and a flow rate controlled filtration (FIG. 4A) using Filter A (Sartorius CPV, 180 cm$^2$) and medium with soy hydrolysate Kerry HyPep 1510 #2 (see Examples 1 to Example 4). The filtrations were carried out for 19 days and reached in this time a volumetric capacity of about 6000-7000 L/m$^2$. The final pressure of the flow controlled filtration was comparable to the pressure of the pressure controlled filtration (see FIG. 4B), and the final specific flow rate of the pressure controlled filtration was comparable to the flow rate of the flow rate controlled filtration (see FIG. 4C). This demonstrates that both control strategies for virus filtration can result in comparable volumetric capacity.

Figure 5A:
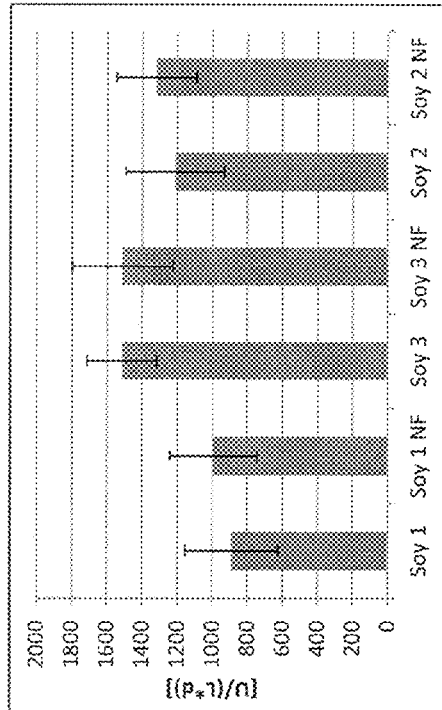
Figure 5B:
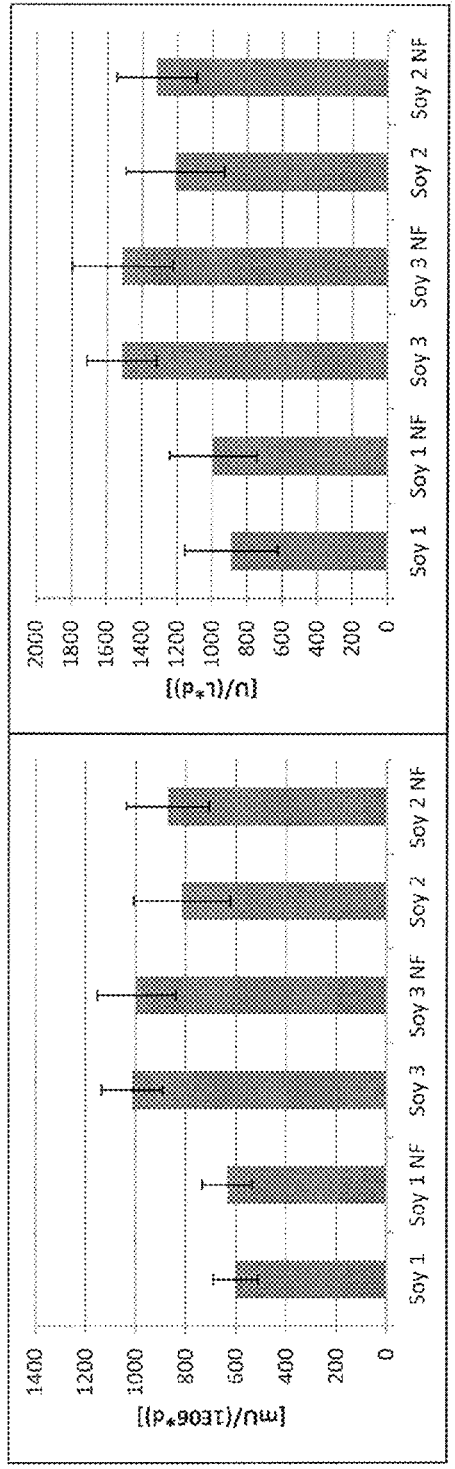
Figure 5C:
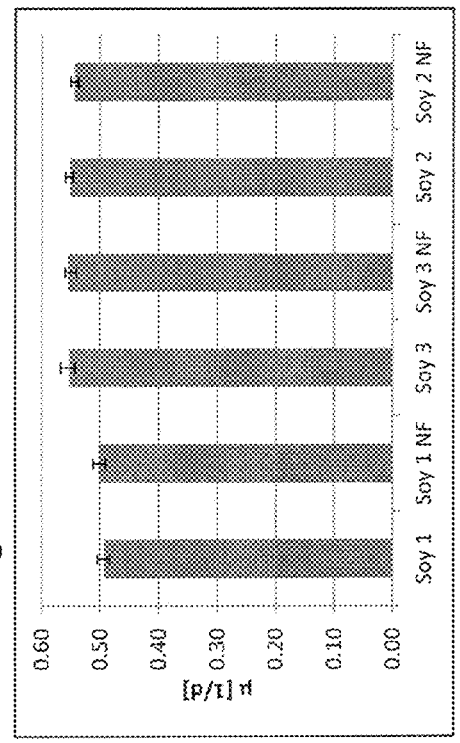

FIG. 5 is showing the results of a 10 L bioreactor experiment using virus filtered medium versus non virus filtered media described in Example 6. Cell culture media were virus filtered batch wise with Filter A prior to start of the experiment. Experiments were carried out in parallel each using cell culture media supplemented with 3 different soy hydrolysates (Kerry HyPep 1510, Lot #1; DOMO SE50 MAF UF, Lot #1 and DOMO SE50 MAF UF, Lot #2). Data were calculated from the last 3 weeks of a 4 week continuous cell culture. No differences between the respective virus filtered media (Soy 1 NF, Soy 3 NF and Soy 2 NF) versus their unfiltered reference (Soy 1, Soy 3 and Soy 2) could be detected for the specific productivity (FIG. 5A), the volumetric productivity (FIG. 5B) and the specific growth rate (FIG. 5C).

Figure 6A:
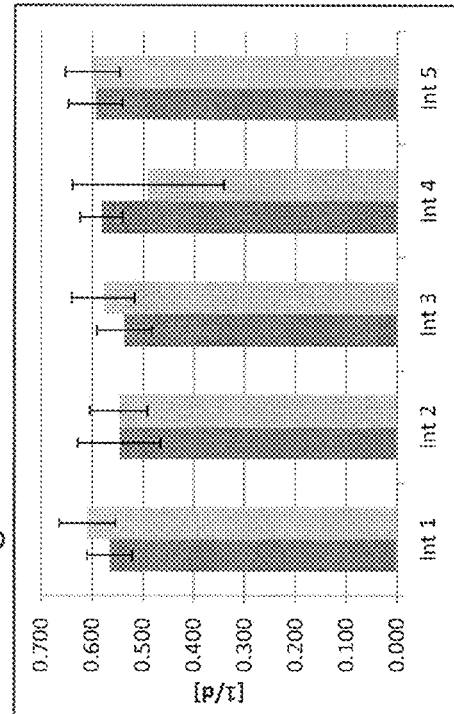
Figure 6B:
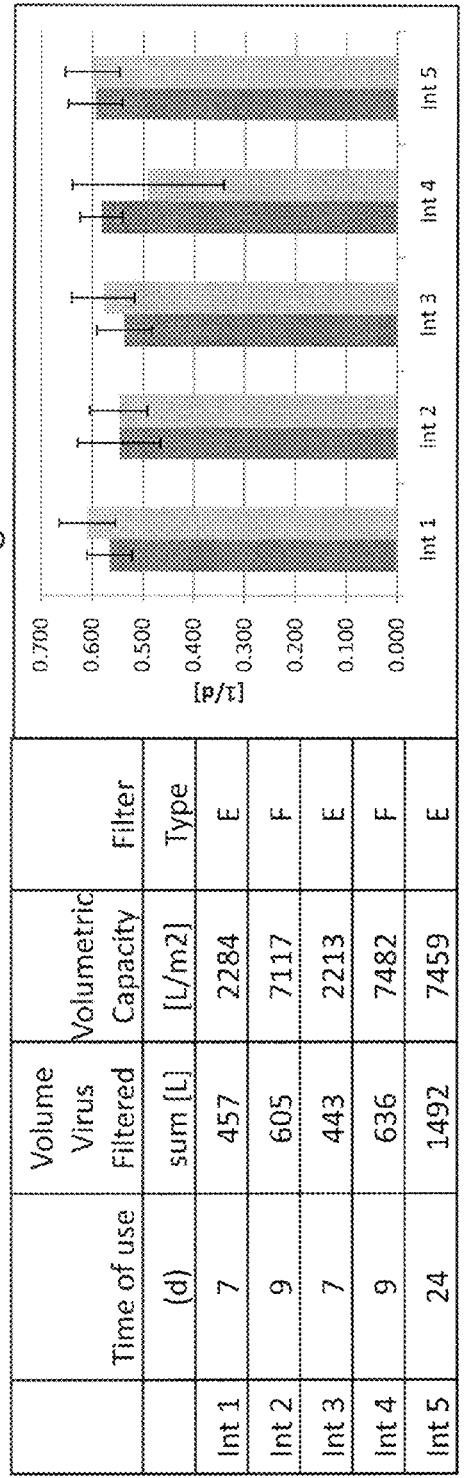
Figure 6C:
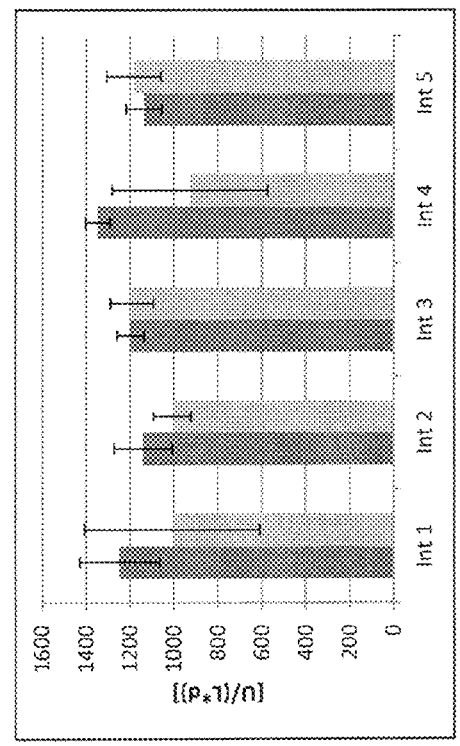

FIG. 6 is showing the results of a 120 L bioreactor experiment using virus filtered medium versus non virus filtered medium described in Example 7. Cell culture media were virus filtered inline of the medium feed line of the bioreactors using alternatively Filter E (Sartorius Virosart CPV, 2000 cm$^2$) and Filter F (Millipore Viresolve NFP 850 cm$^2$) for about 58 days in continuous mode. Time intervals and volumetric capacity of the virus filtered medium feed are shown in FIG. 6A. Data were calculated for the intervals using the different filters. No differences between the respective virus filtered media versus the unfiltered reference could be detected for the specific growth rate (FIG. 6B) and the volumetric productivity (FIG. 6C).

Figure 7:
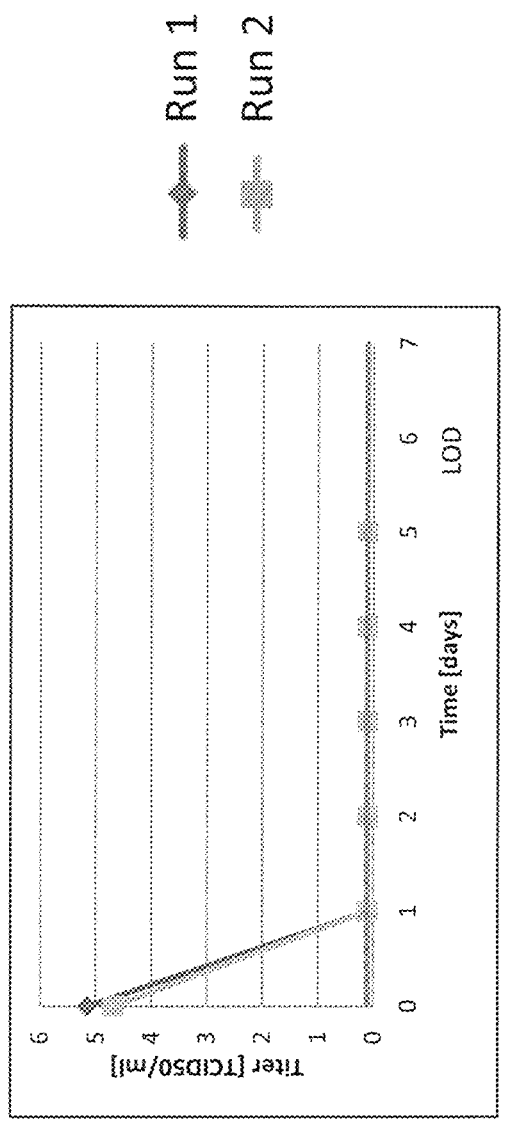

FIG. 7 shows the change of MMV infectivity titer [TCID$_{50}$/mL] found in sequential filtrate samples taken in the course of the filtration of MMV spiked medium containing soy hydrolysate DOMO SE50 MAF#5 UF with Filter G (ASAHI Planova 15N) virus filters (see Example 8). Low level virus break-through was observed within 2 to 3 days. Nonetheless virus removal was seen to be effective.

Figure 8:
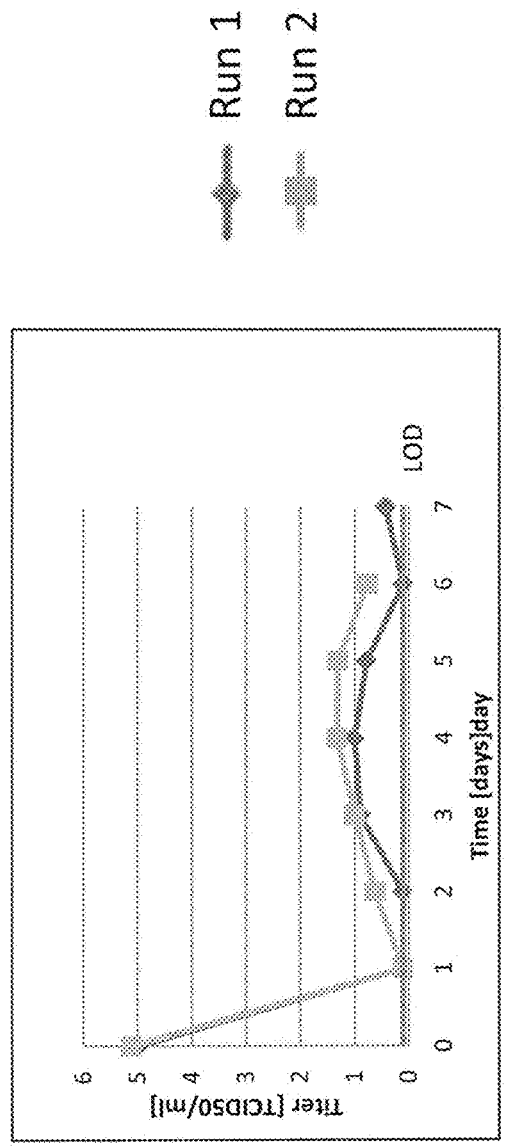

FIG. 8 shows the change of MMV infectivity titer [TCID$_{50}$/mL] found in sequential filtrate samples taken in the course of the filtration of MMV spiked medium containing soy hydrolysate (Run #1 with soy hydrolysate DMV SE50 MAF UF #5; Run #2 with soy hydrolysate DMV SE50 MAF UF #4) with Filter D (Asahi BioEX) virus filters (see Example 9). No virus break-through was observed and virus removal was seen to be effective and complete.

Figure 9:
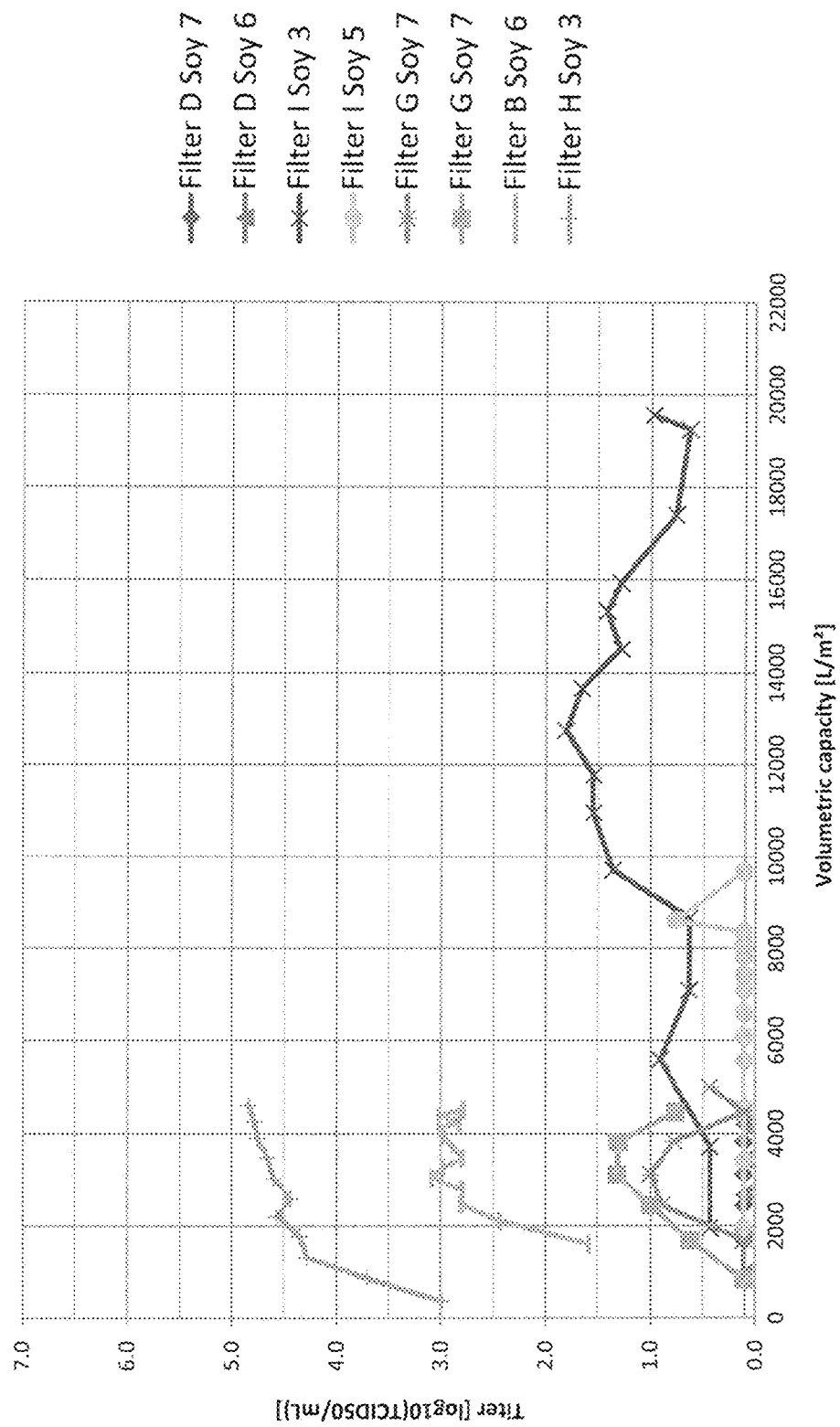

FIG. 9 shows the change of MMV infectivity titer [TCID50/mL] found in sequential filtrate samples taken in the course of the filtration of MMV-spiked media as described in Example 10. No virus break-through was observed for the runs #1 and #2 (Filter D) resulting in effective and complete virus removal from the soy hydrolysate containing media. Low-level virus break-through was observed for the runs Runs #3 and #4 (Filter I) and runs #5 and #6 (Filter G) resulting in effective but not complete virus removal from the soy hydrolysate containing media. More significant virus break-through was observed for the runs #7 (Filter B) and run #8 (Filter H) resulting in reduced virus removal factors at the limit of significance. However with all filters at least in one experiment a minimum overall titer reduction of more than about 1 log TCID50/mL could be achieved.

TABLE 1

Combination of virus filters and soy hydrolysates used in spiking experiments

| Experiment # | Filter | Soy hydrolysate Lot | Overall reduction factor [log$_{10}$(TCID$_{50}$/mL)] |
|---|---|---|---|
| 1 | D | 7 | >5.1 |
| 2 | D | 6 | >4.6 |
| 3 | I | 3 | 4.5 |
| 4 | I | 5 | >5.4 |
| 5 | G | 7 | 4.4 |
| 6 | G | 7 | 4.1 |
| 7 | B | 6 | 1.5 |
| 8 | H | 3 | 1.2 |

Figure 10:
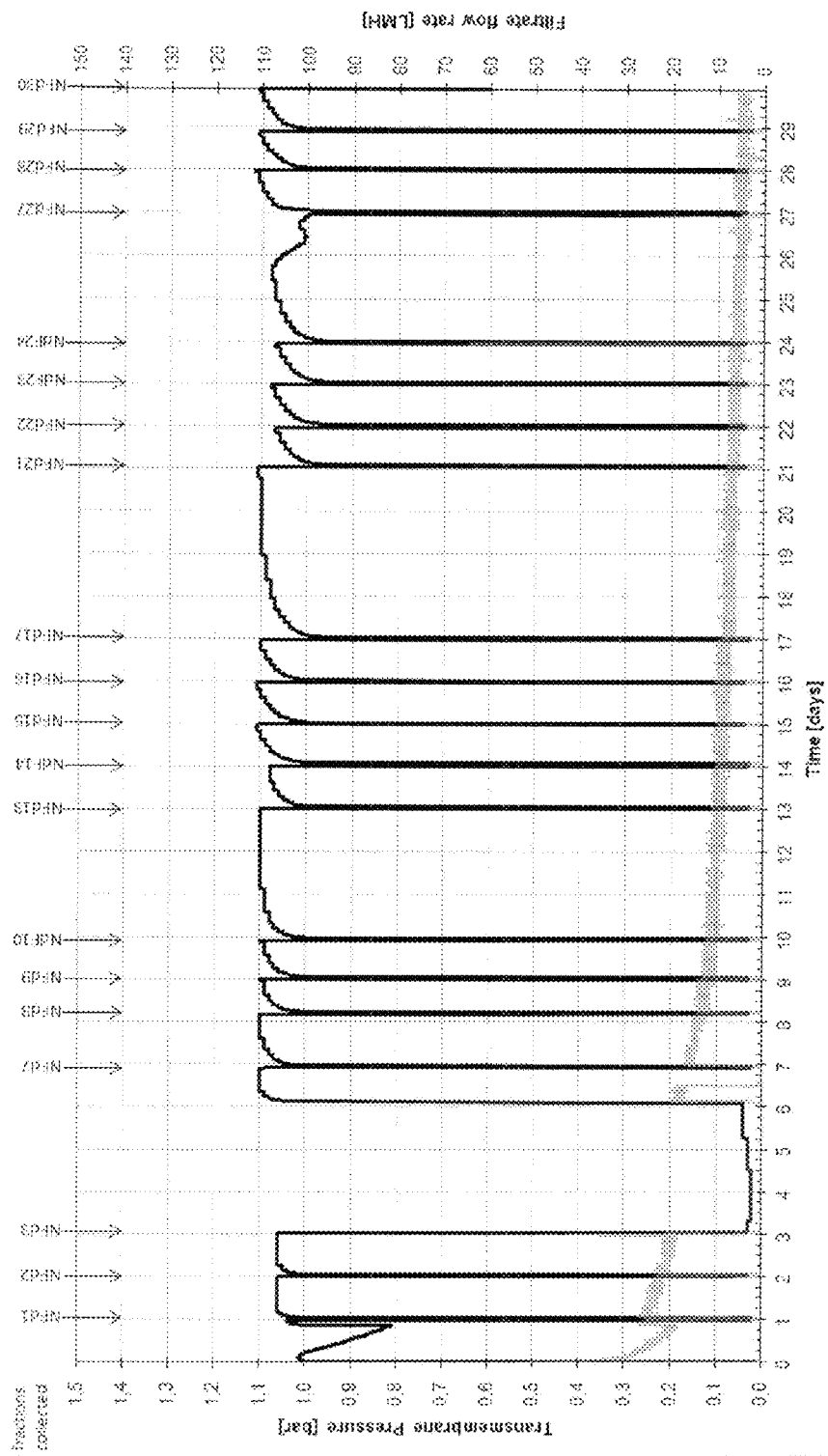

FIG. 10 shows the kinetics of a viral filtration performed as described in Example 11. Pressure was maintained between 0.8 and 1.2 bar (1.1 bar average) except for the intentional pressure and flow interruptions, which simulate the worst case of operational conditions. Initial flow rates of about 38 L/(m$^2$×hr) were achieved, which gradually decreased until the end of the experiment, however, a minimum flow rate of 4 L/(m$^2$×hr) could be maintained. Overall duration including the pressure interruptions was 30 days. Approximately 6500 L/m$^2$ were passed over the filter.

FIG. 11 shows the change of MMV infectivity titer [log$_{10}$(TCID$_{50}$/mL)] found in sequential filtrate samples taking in the course of the filtration of MMV-spiked media as described in example 11. No virus break-through was observed in any of the 20 fractions assayed. Virus loads ranged from <0.9[log$_{10}$(TCID$_{50}$)] to <2.8[log$_{10}$(TCID$_{50}$)] depending on fraction volume. The total virus load in the filtrates was <3.0[log$_{10}$(TCID$_{50}$)] which—when subtracted from the initial virus load of the spiked material (i.e. 8.5[$\log_{10}$(TCID$_{50}$)])—results in an overall virus reduction factor of >5.5 $\log_{10}$. This was seen to be effective and complete.

DETAILED DESCRIPTION OF THE INVENTION

The present invention provides a method for removing a viral contaminant from a preparation, being a cell culture medium or at least a component of a cell culture medium. The method comprises subjecting said preparation to filtration for at least about 24 hours through a virus filter having an effective pore size of maximum 75 nm.

Further, the invention relates to the use of a virus filter having an effective pore size of maximum 75 nm in a filtration for at least 24 hours for the removal of viral contaminant from a preparation, being a cell culture medium or at least a component of a cell culture medium.

In addition, the invention relates to the use of a preparation, being a cell culture medium or at least a component of a cell culture medium obtainable according to any method of the present invention for cell culture; pharmaceutical, diagnostic and/or cosmetic preparations as well as in food preparations.

In all embodiments of the invention the preparation is subjected to virus filtration, the virus filtration or the use of the virus filter is performed for at least about 24 hours, about 48 hours, about 72 hours, about 4 days, about 5 days, about 6 days, about 7 days, about 1 week, about 2 weeks, about 3 weeks, about 4 weeks, about 1 month, about 2 months, about 3 months, about 4 months, about 5 months, about 6 months or about 7 months. Further in one embodiment the preparation is subjected to virus filtration or the virus filtration is performed for about 1 week to about 3 weeks, about 2 weeks to about 3 weeks, about 1 week to about 4 weeks about 2 weeks to about 4 weeks, about 1 week to about 7 months, about 1 months to about 5 months, about 2 months to about 5 months, about 2 months to about 4 months, about 2 months to about 3 months or at least about 24 hours up to about 7 months or about 48 hours up to about 5 months or about 72 hours up to about 3 months. Further, in one embodiment the preparation is subjected to virus filtration or the virus filtration is performed for longer than about 48 hours up to about 7 months, preferably about one week to about 5 months or about 3 weeks to about 3 months or about 2 months to about 3 months.

The method according to the invention can operate at a volumetric capacity of at least about 2000 L/m$^2$, or at least about 3000 L/m$^2$, or at least about 4000 L/m$^2$, or at least about 5000 L/m$^2$, at least about 7500 L/m$^2$, at least about 10000 L/m$^2$, or at least about 20000 L/m$^2$. In this respect the "volumetric capacity" refers to the volume of solution that can be filtered through a specified area of the virus filter membrane before filtrate flow is reduced or the back pressure is increased to undesirable operating conditions due to the clogging of the filter membrane.

It is contemplated that the present invention including all embodiments can be employed alone or in conjunction with other approaches known in the art for minimizing viral contamination, e.g. screening, sourcing, detection, viral inactivation, adsorptive retention, etc. The present methods target the entry of unwanted viral agents through the preparation, being a cell culture medium or at least a component of a cell culture medium, early in the production process and provide a viral reducing mechanism. Advantages of the present invention include ease of implementation on a large-scale basis, reduced filter membrane area needed to process a given volume of a preparation, being a cell culture medium or at least a component of a cell culture medium, the reduced cost ensuing therefrom. In particular virus filtration of preparations according to the invention is easy to integrate into continuous manufacturing processes, e.g. continuous cell culture processes like perfusion or chemostat like bioreactor systems.

The term "temperature" as used herein concerns the temperature of the filtered preparations according to the invention, e.g. a cell culture medium or buffer, at the time it passes through the virus filter. In one embodiment according to the invention the temperature ranges from about 2° C. to about 60° C. In one embodiment the lower limit of the temperature range is about 2° C., about 4° C., about 8° C., about 10° C., about 15° C., about 20° C., about 22° C., about 25° C., about 30° C., about 37° C. or about 40° C. The upper limit of the temperature range according to the invention is about 10° C., about 20° C., about 22° C., about 25° C., about 30° C., about 37° C., about 40° C., about 50° C. or about 60° C. In one embodiment the temperature is in a range from about 4° C. to about 45° C., or at a temperature range from about 10° C. to about 40° C., or from about 20° C. to about 40° C., or from about 30° C. to about 37° C. Also in one embodiment the temperature is ambient temperature that is a range from about 20° C. to about 30° C. Of course, also embodiments are preferred where the preparations are subjected to filtration without any further heating or cooling of the preparations. Therefore, in a further embodiment a temperature of about 10° C. to about 30° C. is used depending from the temperature of the respective place at which the filtration is performed. In another embodiment, temperatures of about 30° C. to about 37° C. are used, e.g. by preheating of the liquid preparation prior to filtration. The filtrate resulting from this filtration of a preparation can be continuously fed to a bioreactor.

In one embodiment of the invention filtration is performed at a pressure ranging from about 100 mbar to about 4000 mbar, or from about 200 mbar to about 3500 mbar. In one embodiment, virus filtration is performed at a pressure range, wherein the lower limit is about 100 mbar, about 200 mbar, about 500 mbar, about 1000 mbar, about 1200 mbar, about 1500 mbar, about 2000 mbar, about 2500 mbar or about 2800 mbar. The upper limit is about 1200 mbar, about 1500 mbar, about 2000 mbar, about 2500 mbar, about 2800 mbar or about 3000 mbar. In one embodiment, filtration is performed at a pressure ranging from about 1000 to about 4000 mbar, about 1500 to about 3500 mbar, 1700 mbar to about 3300 mbar or about 1000 mbar to about 2000 mbar.

Temperature and pressure adjustments may be utilized in further embodiments of the invention to regulate the specific flow rate and the volumetric capacity. Further improvements in the volumetric capacity and the time span of use of the virus filter can be obtained by regulating other process parameters, such as filtration pressure and temperature. For instance, it has turned out that in some embodiments it is preferred to subject the preparation to filtration at a temperature of about 10° C. to about 40° C. at a pressure of about 1000 mbar to about 2000 mbar.

Preliminary filtration experiments have demonstrated the influence of temperature of the preparations to be filtered on the specific flow rate. An about 50 to about 100% increase of flow rate was observed when increasing the filtration temperature from a preparation according to the invention having a storage temperature of about 4° C. to temperatures of from about 18° C. to about 37° C. However, all these embodiments are within the scope that the use of filtration for at least about 24 hours effects that the capacity of the used costly virus filters can be better exploited leading to an 2 to 100-fold increase of the volumetric capacity while maintaining the filter integrity.

In one preferred embodiment the method for removing a viral contaminant from a preparation, being a cell culture medium or at least a component of a cell culture medium, comprises the step of subjecting said preparation to filtration for at least about 10 days to about 2 months through a virus filter having an effective pore size of maximum 75 nm at a pressure of about 1000 mbar to 2000 mbar and a temperature of 10° C. to 40° C. having a volumetric capacity of at least 2000 L/m². Of course, all other parameters can be combined also with this embodiment. In addition, as a further preferred embodiment said method is performed in a continuous filtration mode, wherein the preparation is preferred a cell culture medium, e.g. a cell culture medium comprising a soy hydrolysate or a cell culture medium comprising animal derived components, wherein the filtrate is continuously fed to a bioreactor, in particular a chemostat reactor. In another embodiment this embodiment can further be performed using at least 2 virus filters arranged in parallel or in series.

It is contemplated that the virus filtration methods as described herein can be used to reduce viral contamination from any preparation being a cell culture medium or a component of a cell culture medium, i.e. a medium and buffers suitable for growth of animal cells, and preferably mammalian cells, in in vitro cell culture. Typically, culture medium contains a buffer, salts, energy source, amino acids, vitamins and trace essential elements.

The term "preparation" also includes any component being a possible part of a cell culture medium in the sense of the present invention and capable of supporting growth of the appropriate cell in culture. Said preparations include e.g. a buffer or solutions of at least one amino acid or protein; solutions of at least one vitamin; solutions of at least one organic or inorganic salt; or solutions comprising at least one source of carbohydrates or sugars.

In the context of the present invention "Log reduction value" (LRV) is a measure of a membrane's efficiency in retaining a particle such as bacteria or virus, defined as the logarithm (base 10) of the ratio of said particle count in the feed stream to the particle count in the virus filter membrane permeate. The LRV value is specific to a given type of particle. In one embodiment according to the invention the virus filter achieves at least a 1 $Log_{10}$ reduction value (LRV) for a viral contaminant, or at least a 2 $Log_{10}$ reduction value (LRV) for a viral contaminant, or at least a 3 $Log_{10}$ reduction value (LRV) for a viral contaminant, or at least a 4 $Log_{10}$ reduction value (LRV) for a viral contaminant, or at least a 5 $Log_{10}$ reduction value (LRV) for a viral contaminant, or at least a 6 $Log_{10}$ reduction value for viral contaminant, or at least a 7 $Log_{10}$ reduction value for viral contaminant, or at least a 8 $Log_{10}$ reduction value for viral contaminant, preferably at least a 4 $Log_{10}$ reduction value (LRV) for a viral contaminant. Of course, it is evident for a skilled person in the art, that any $Log_{10}$ reduction value (LRV) of a viral or potential viral contaminant of the preparation to be filtered is beneficial in order to improve the safety of a production process. Therefore, especially this parameter can be combined with all other parameters that are used in the method of the present invention.

"Flux," as used herein is interchangeable used with "specific flow rate" or "flow rate" is a measure used to characterize membranes, refers to the rate of filtrate flow (expressed in the volume or weight of solution that permeates through the virus filtration membrane per filter area and time, e.g. $L/(m^2 \times hr)$. In the context of the invention the term "specific" means within a defined time, however, when only "flow rate" is used, also from the units of this parameter it is evident that the "specific flow rate" is meant. As abbreviation of the quantity "volume" given in the unit "liter" "l" oder "L" is used interchangeably. The specific flow rate within the method of the present invention may vary within a range or remain substantially fixed throughout the duration of the filtration process using a given virus filter. In one embodiment of the present invention the specific flow rate may range from about 5 $L/(m^2 \times hr)$ to about 500 $L/(m^2 \times hr)$ for at least 24 hours up to about 7 months. The lower limit for the flux may be about 5 $L/(m^2 \times hr)$ or about 10 $L/(m^2 \times hr)$. The upper limit may be about 25 $L/(m^2 \times hr)$, about 75 $L/(m^2 \times hr)$, about 100 $L/(m^2 \times hr)$, about 200 $L/(m^2 \times hr)$, about 250 $L/(m^2 \times hr)$, about 300 $L/(m^2 \times hr)$ or about 500 $L/(m^2 \times hr)$. The flux may further range from about 5 $L/(m^2 \times hr)$ to about 100 $L/(m^2 \times hr)$, about 10 $L/(m^2 \times hr)$ to about 100 $L/(m^2 \times hr)$ or about 10 $L/(m^2 \times hr)$ to about 25 $L/(m^2 \times hr)$.

"Batch filtration," otherwise known as "batch wise filtration" or filtration done in batch mode, refers herein to a process wherein a specific total amount or volume of a preparation, being a cell culture medium or at least a component of a cell culture medium, is filtered through a virus filter in one batch dependent on the capacity of the virus filter and wherein the filtration process is finalized before the filtrate is directed or fed to the process in which it is used or consumed.

The term "continuous filtration" or "online filtration" or "in line filtration" refers to a filtration process, wherein the specific total amount or volume of a preparation, being a cell culture medium or at least a component of a cell culture medium, is filtered through the virus filter continuously dependent on the capacity of the virus filter and wherein the filtration process is still going on when the filtrate is already directed or fed to the process in which it is used or consumed.

All embodiments of the present invention may be performed using batch or continuous filtration. The beneficial effect of the invention is already achieved by subjecting a preparation, being a cell culture medium or at least a component of a cell culture medium, to filtration for at least 24 hours through a virus filter having an effective pore size of maximum 75 nm in order to remove a viral contaminant from said preparation.

In a preferred embodiment according to the invention the method for removing a viral contaminant from a preparation, being a cell culture medium or at least a component of a cell culture medium, wherein said preparation is subjected to filtration for at least about 24 hours through a virus filter having an effective pore size of maximum 75 nm, is performed as continuous filtration. This mode of operation has the advantage that the produced filtrate of the preparation can be directly and continuously fed to the process where it is used or consumed. In a further preferred embodiment the virus filtered preparation, being a cell culture medium or at least a component of a cell culture medium, can directly and continuously feed a bioreactor, more preferably a large scale bioreactor used in a continuously fed cell culture process, e.g. a chemostat process, a perfusion process or a fed batch process. This embodiment is performed in one embodiment using a pressure of about 1000 mbar to 2000 mbar and a temperature of 10° C. to 40° C., wherein the volumetric capacity is at least 2000 L/m² or at least 5000 L/m². In addition, it is further preferred that the virus filtration of the preparation is performed for at least about 24 hours or about 48 hours up to about 7 months, more preferred for at least about one week up to about 5 months and most preferred for at least about one to about 3 weeks or about 3 weeks to about 3 months and even most preferred at least about 2 to about 3 months. Of course, all other parameters can be combined with this embodiment. In addition, it is preferred that the preparation to be filtered is a cell culture medium and the mode of filtration is a continuous mode filtration.

Of course, it is known by a skilled person in the art that the virus filtered preparations obtainable according to any of the methods according to the invention may also be directed or fed to other production processes relating to cell culture; pharmaceutical, diagnostic and/or cosmetic preparations as well as food preparations. Also in those embodiments a continuously filtration of the preparations is preferred.

Hence, the invention also relates to the use of a preparation, being a cell culture medium or at least a component of a cell culture medium obtainable according to any of the methods according to the invention for cell culture; pharmaceutical, diagnostic and/or cosmetic preparations as well as in food preparations.

In some embodiments, the cell culture medium to be virus filtered is sterile, or otherwise pretreated. In some embodiments the cell culture medium comprises animal proteins or serum or other animal derived components, or is animal protein-free, or serum-free, or free of animal derived components, or possess any combination of the foregoing characteristics. In other embodiments, the cell culture medium comprises varying concentrations and species of plant or microbial derived hydrolysates, especially soy hydrolysates. In a preferred embodiment the cell culture medium is an animal protein-free medium comprising varying concentrations of at least one soy hydrolysate. However, it has to be emphasized that the method according to the invention is especially suitable for virus filtration of preparations comprising animal protein or serum or other animal derived components in order to further improve the virological safety of those preparations, in particular when used in cell culture processes, in pharmaceutical, diagnostic and/or cosmetic preparations as well as in food preparations.

"Cell culture medium" is defined, for purposes of the invention, as a medium suitable for growth of cells, and preferably animal cells, more preferably mammalian cells, in in vitro cell culture. Any medium capable of supporting growth of the appropriate cells in cell culture can be used. The cell culture medium according to the invention may be based on any basal medium such as DMEM, Ham's F12, Medium 199, McCoy or RPMI generally known to the skilled worker. The basal medium may comprise a number of ingredients, including amino acids, vitamins, organic and inorganic salts, and sources of carbohydrate, each ingredient being present in an amount which supports the cultivation of a cell which is generally known to the person skilled in the art. The medium may contain auxiliary substances, such as buffer substances like sodium bicarbonate, antioxidants, stabilizers to counteract mechanical stress, or protease inhibitors. If required, a non-ionic surfactant such as mixtures of polyethylene glycols and polypropylene glycols (e.g. Pluronic F68®, SERVA) can be added as a defoaming agent.

As used herein, an "animal protein-comprising medium" is a cell culture medium that comprises any protein that has been derived from a human source or an animal source.

As used herein, a "protein-free medium" is a cell culture medium that is free of any protein that has been derived from a human source or an animal source.

The term "animal protein-free cell culture medium" according to the invention refers to a medium that does not contain proteins and/or protein components from higher multicellular non-plant eukaryotes. Typical proteins that are avoided are those found in serum and serum-derived substances, such as albumin, transferrin, insulin and other growth factors. The animal protein free cell culture medium is also free of any purified animal derived products and recombinant animal derived products as well as protein digests and extracts thereof or lipid extracts or purified components thereof. Animal proteins and protein components are to be distinguished from non-animal proteins, small peptides and oligopeptides obtainable from plants (usually 10-30 amino acids in length), such as soy bean, and lower eukaryotes, such as yeast which may be included into the animal protein free cell culture medium according to the invention.

The term "hydrolysate" includes any digest of an animal derived or plant derived source material or extracts derived from yeast or bacteria. In the cell culture medium according to the invention "soy hydrolysate" can be comprised that may be a highly purified soy hydrolysate, a purified soy hydrolysate or crude soy hydrolysate.

The term "serum-comprising" as applied to medium includes any cell culture medium that does contain serum.

The term "serum-free" as applied to medium includes any cell culture medium that does not contain serum. By "serum free", it is understood that the medium has preferably less than 0.1% serum and more preferably less than 0.01% serum. The term "serum" refers to the fluid portion of the blood obtained after removal of the fibrin clot and blood cells.

In some embodiments, the filtrate or the flow of the filtrate obtained from the filtration process is fed to a large-scale cell culture and bioreactor respectively. A "large-scale" cell culture, as used herein, refers to a cell culture at a scale of at least about 100 L, at least about 200 L, at least about 300 L, at least about 400 L, at least about 500 L, at least about 1000 L, at least about 1500 L, at least about 2000 L, at least about 2500 L, at least about 3000 L, at least about 4000 L, at least about 5000 L, at least about 7500 L, at least about 10000 L or at least about 20000 L. In a preferred embodiment the filtrate flow obtained in any method according to the invention is fed to a bioreactor used in a chemostat process, a perfusion process or a fed batch process, preferably by continuous filtration.

The cell culture contemplated herein may be any cell culture independently of the kind and nature of the cultured cells and the growth phase of the cultured cells, e.g. adherent or non-adherent cells; growing, or growth-arrested cells.

The term "sterile," as used according to the invention, refers to a substance that is free, or essentially free, of microbial and/or viral contamination. In this respect the "contaminant" means a material that is different from the desired components in a preparation being a cell culture medium or at least a component of a cell culture medium. In the context of "sterile filtration", the term sterile filtration is a functional description that a preparation is filtered through a sterile filter to remove bacterial and/or mycoplasma contaminants.

The term "virus filtration" is used herein interchangeably with the term "nanofiltration" and means that for the filtration process a virus filter is used having a defined effective pore size. In general those filters are dedicated to remove viruses.

The viral contaminant targeted for removal by filtration according to all methods of the invention may be any virus presently known in the art or to be discovered in the future. This definition also includes a potential viral contaminant to be removed by filtration and also includes that more than one virus is removed by the methods of the present invention. For example, the viral contaminant or potential viral contaminant can be a member of the viral families of Orthomyxoviridae, Arenaviridae, Paramyxoviridae, Rhabdoviridae, Coronaviridae, Flaviviridae, Picornaviridae, Togaviridae, Arteriviridae, RetParvoviridae, Bunyaviridae, Caliciviridae, Retroviridae, Reoviridae, Circoviridae, Adenoviridae, Poxviridae, Herpesviridae, Iridoviridae or Reoviridae. More specifically, the viral contaminant may be any of the group consisting of canine parvoviridae (CPV), minute virus of mice (MVM), Cache Valley virus, Bunyamwera virus, Northway encephalitis virus, Influenza NB virus, Junin virus, Parainfluenza virus 1/2/3, Simian virus 5, Mumps virus, Bovine respiratory syncytial virus, Sendai virus, Newcastle disease virus, Pneumonia virus of mice, vesicular stomatitis virus, Rabies virus, Bovine coronavirus, Murine hepatitis virus, Yellow fever virus, West Nile virus, Dengue virus, Tick borne encephalitis virus, St. Louis encephalitis virus, Vesivirus 2117, Encephalomyocarditis virus, Coxsackie virus B-3, Theiler's mouse encephalitis virus, Foot and mouth disease virus, Bovine enterovirus, Porcine enterovirus, Semliki Forest virus, Sindbis virus, Rubella virus, Japanese encephalitis virus, Eastern equine encephalitis virus, Porcine reproductive and respiratory syndrome virus, Foamy virus, Reovirus 1/2/3, Avian reovirus, Rotavirus, Porcine circovirus 1, Adenovirus, Pseudorabies virus, Murine gammaherpes 68, Herpes simplex virus 1, Frog virus 3, minute virus of mice-cutter (MVMc), bluetongue virus (BTV), Epizootic haemorrhagic disease virus (EHDV), bovine viral diarrhea virus (BVDV), porcine parvovirus (PPV), encephalomyocarditis virus (EMCV), Reovirus 3, and murine leukemia virus (MuLV), Hepatitis A, polio, or Parvoviridae B19.

The term "virus filter," is used interchangeably herein with the terms "virus-retentate filter", "viral filter" and "nanofilter" and refers generally to a filter which characteristics as a whole make it suitable for virus retention having an effective pore size to fulfill this function. These characteristics include, by way of example, membrane attributes such as morphology, pore shape, pore density, and uniformity, effective pore size, membrane thickness, etc. The virus filter membranes useful in the present invention encompass membranes that operate by size exclusion and charge, possibly in combination with adsorptive retention. Size exclusion and adsorptive retention mechanisms are not necessarily exclusive of one another and a filter may well employ one or more mechanisms.

The virus filter as defined in the present invention and used in one embodiment of the present invention is characterized by having a membrane with an effective pore size of maximum 75 nm. In one embodiment according to the invention the lower limit of the effective pore size is about 5 nm, about 10 nm, about 15 nm, about 20 nm, about 25 nm, about 30 nm, about 35 nm, about 50 nm or about 60 nm. In said embodiment according to the invention the upper limit of the effective pore size is about 10 nm, about 15 nm, about 20 nm, about 25 nm, about 35 nm, about 50 nm, about 60 nm or about 75 nm. In some embodiments of the invention, the virus filter has an effective pore size from about 5 to about 75 nm or from about 10 to about 75 nm or from about 15 to about 75 nm or from about 20 to about 75 nm or from about 15 to about 50 nm or from about 15 to about 35 nm.

Effective pore size, as used herein, is a characteristic of a membrane and refers to the size of a particle which can be effectively retained by the membrane, considering that the level of effectiveness is described by a logarithmic reduction factor of a particle of such size.

The virus filter used in the methods of the present invention can be any filter having a construction sufficient to withstand a volumetric capacity of at least about 2000 L/m$^2$, or at least about 3000 L/m$^2$, or at least about 4000 L/m$^2$ or at least about 5000 L/m$^2$, or at least about 7500 L/m$^2$, or at least about 10000 L/m$^2$ or at least about 20000 L/m$^2$, or which can be operated for a time span of more than about 24 hours up to about 7 months or preferably for at least about 48 hours, about 72 hours, about 4 days, about 5 days, about 6 days, about 7 days, about 1 week, about 2 weeks, about 3 weeks, about 4 weeks, about 1 month, about 2 months, about 3 months, about 4 months, about 5 months, about 6 months or about 7 months.

Of course, if more than one filter is used in a method according to the invention also different types of virus filters can be used and combined in the filtration process, preferably in parallel or in series.

Exemplary virus filter comprise a single or multilayer membrane and are constructed of material such as polyvinylidene fluoride (PVDF), cellulose, modified cellulose, e.g. cuprammonium regenerated cellulose hollow fibers or polyethersulfone. The membranes of the virus filters may have a neutral, negative, or positive charge. The membranes may be ionic membranes, i.e. they may contain cationic or anionic groups, but neutral membranes may be preferred depending on the pH conditions. The virus filter membranes may be selected from hydrophobic and hydrophilic membranes. In a preferred embodiment the membrane of the virus filter used in the method according to the invention is made from polyvinylidene fluoride (PVDF) or polyethersulfone.

Manufacturers of exemplary filters having demonstrated ability to remove viruses include, without exclusion, Asahi/Planova, PALL, Millipore, Sartorius, Gambro, and Amersham/AG Technology. Filters suitable for use in the present invention include, without limitation, Asahi's Planova 15 N filter (Asahi Kasei Corporation, Planova Division), Planova 20 N filter (Asahi Kasei Corporation, Planova Division), Planova 35 N filter (Asahi Kasei Corporation, Planova Division), and the BioEX filter (Asahi Kasei Corporation, Planova Division).

Of course, it is desirable that the filter used in one of the methods of the present invention is autoclavable and/or autoclaved and/or otherwise sterilized before use. However, all other possibilities to ensure the sterility of the used virus filter are suitable to perform the invention. Furthermore it is desirable that the filter can be integrity tested prior to use and/or after use. In a preferred embodiment, in the method according to the invention an autoclaved, integrity tested virus filter is used having a membrane of polyvinylidene fluoride (PVDF) or polyethersulfone.

"Filtrate", used interchangeably herein with the term "permeate," refers to the solution that crosses a filter or membrane as well as the solution that has crossed a filter or membrane.

"Retentate", as used herein, refers to the component of the solution that is retained and does not cross a filter or membrane as well as that has not crossed a filter or membrane.

The virus filtration equipment useful in the present invention comprises at least one virus filtration membrane element dividing the feed into a pre and post filter section. The filtration equipment typically also includes means for controlling the pressure and flow, such as pumps and valves and flow and pressure meters and density meters. The equipment may also include several filtration membrane elements in different combinations, arranged in parallel or series or both.

The filtration flux varies in accordance with the pressure. In general, at a normal operation range, the higher the pressure, the higher the flux. The flux also varies with the temperature. An increase of the operating temperature increases the flux. However, with higher temperatures and with higher pressures there is an increased tendency for a membrane rupture. For inorganic membranes, higher temperatures and pressures and higher pH ranges can be used than for polymeric membranes.

For a skilled person in the art it is unambiguously evident that instead of a virus filter according to the invention a filter can be used having a molecular weight cut-off of less than about 5000 Daltons or less than about 1000 Daltons in order to remove also viruses. In this context "Molecular weight cut-off" (MWCO) is a membrane characteristic of a filter that specifies the average molecular weight of solutes, however also particles or viruses will not permeate the membrane of this filter.

The pH value in the virus filtration process of the present invention can be set at any range necessary to preserve the stability and functionality of the preparation being filtered, preferably a cell culture medium or buffer. For example, the pH value may be set at about 1 to about 10, preferably about 2 to about 8 or about 3 to about 7, preferably about 6.8 to about 8 or most preferably at about 7.0 to about 7.45 (physiological pH value).

It is also contemplated that the method according to the invention may be integrated into a system downstream of a sterilizing grade filter that removes bacteria contaminant and thereby yield a sterile feed stream of a preparation that can be the "starting preparation", i.e. the preparation being used in any method according to the invention.

In one embodiment the method of the invention may be performed using two or more filters arranged in series. This has the advantage of augmenting virus clearance capacity and safeguard against potential virus filter failure or breakthrough. In alternative embodiments, filtration is performed using two or more virus filters arranged in parallel, thereby permitting virus filter replacement without disrupting a continuous process and preventing unforeseen medium holds, e.g. due to clogging.

In still other embodiments, filtration is performed using at least two filters arranged in parallel in a piping system comprising a Y-shaped junction, wherein each filter is in fluid communication with a branch of the Y-shaped junction and a preparation supply source. In some embodiments, the Y-shaped junction comprises a connector. In other embodiments, filtration is performed using a setup containing a plurality of filters arranged both in series and in parallel. Especially useful in the context of the present invention is an arrangement, wherein at least a second filter is arranged in parallel in connection with other parallel filters or filters arranged in series in order to have the possibility to replace one of the filters without stopping the filtration process for maintenance reasons.

In some embodiments, the filter is subjected to an integrity test prior to use. The integrity test may take the form of an air-water diffusion based test, wherein air is directed to the filter and the filter then submerged in sterile water and examined for bubbles, which would indicate a leak in the filter.

In one embodiment, the virus filter or the virus filter membrane may be pretreated before the virus filtration procedure, e.g. by washing with a washing agent, in particular with an acidic washing agent, an alkaline washing agents and/or ethanol.

In one embodiment of the invention also tangential flow filtration may be performed in the method according to the invention. In the context of the present invention "tangential flow filtration," is used interchangeably herein with the term "crossflow filtration." In tangential flow mode, the liquid flow path on the upstream side of the filter is directed roughly parallel to or tangential to or across the filter surface. Passage of the permeate is facilitated by restricting the flow of retentate relative to feed, resulting in backpressure to the system and permitting permeate migration through the filter membrane. The constant sweeping current across the membrane surface has the effect of minimizing clogging by contaminants in the product being filtered. Any virus filter is suitable that achieves at least a 1 $Log_{10}$ reduction value (LRV) for a viral contaminant, or at least a 2 $Log_{10}$ reduction value (LRV) for a viral contaminant, or at least a 3 $Log_{10}$ reduction value (LRV) for a viral contaminant, or at least a 4 $Log_{10}$ reduction value (LRV) for a viral contaminant, or at least a 5 $Log_{10}$ reduction value (LRV) for a viral contaminant, or at least a 6 $Log_{10}$ reduction value for viral contaminant, or at least a 7 $Log_{10}$ reduction value for viral contaminant, or at least a 8 $Log_{10}$ reduction value for viral contaminant, preferably at least a 4 $Log_{10}$ reduction value (LRV) for a viral contaminant. All log reduction factors may apply for any of the effective pore sizes of maximum 75 nm of the virus filter. In one embodiment according to the invention the lower limit of the effective pore size of the virus filter is about 5 nm, about 10 nm, about 15 nm, about 20 nm, about 25 nm, about 30 nm, about 35 nm, about 50 nm or about 60 nm. In said embodiment according to the invention the upper limit of the effective pore size of the virus filter is about 10 nm, about 15 nm, about 20 nm, about 25 nm, about 35 nm, about 50 nm, about 60 nm or about 75 nm. In some embodiments of the invention, the virus filter has an effective pore size from about 5 to about 75 nm or from about 10 to about 75 nm or from about 15 to about 75 nm or from about 20 to about 75 nm or from about 15 to about 50 nm or from about 15 to about 35 nm.

In some embodiments of the present invention normal flow filtration is used. "Normal flow filtration", used interchangeably herein with the terms "dead end," "single pass," and "direct flow filtration," refers to a virus filter filtration process wherein the liquid flow path is directed usually perpendicular to the filter surface, dependent on the construction of the filter module the fluid stream could also be directed tangential to the filter membrane, however in contrast to crossflow filtration, no recirculation of retentate is applied, which means that the specific flow rate before and after the filter is identical. Any virus filter is suitable that achieves at least a 1 $Log_{10}$ reduction value (LRV) for a viral contaminant, or at least a 2 $Log_{10}$ reduction value (LRV) for a viral contaminant, or at least a 3 $Log_{10}$ reduction value (LRV) for a viral contaminant, or at least a 4 $Log_{10}$ reduction value (LRV) for a viral contaminant, or at least a 5 $Log_{10}$ reduction value (LRV) for a viral contaminant, or at least a 6 $Log_{10}$ reduction value for viral contaminant, or at least a 7 $Log_{10}$ reduction value for viral contaminant, or at least a 8 $Log_{10}$ reduction value for viral contaminant, preferably at least a 4 $Log_{10}$ reduction value (LRV) for a viral contaminant. All log reduction factors may apply for any of the effective pore sizes of maximum 75 nm of the virus filter. In one embodiment according to the invention the lower limit of the effective pore size of the virus filter is about 5 nm, about 10 nm, about 15 nm, about 20 nm, about 25 nm, about 30 nm, about 35 nm, about 50 nm or about 60 nm. In said embodiment according to the invention the upper limit of the effective pore size of the virus filter is about 10 nm, about 15 nm, about 20 nm, about 25 nm, about 35 nm, about 50 nm, about 60 nm or about 75 nm. In some embodiments of the invention, the virus filter has an effective pore size from about 5 to about 75 nm or from about 10 to about 75 nm or from about 15 to about 75 nm or from about 20 to about 75 nm or from about 15 to about 50 nm or from about 15 to about 35 nm.

As those of ordinary skill in the art would appreciate, all embodiments of the invention can be implemented with the aid of any available system technically useful for the purpose, e.g. a variable-speed or fixed-speed peristaltic pump, a centrifugal pump, etc. Any kind of pressurized vessel or other container can be used to generate flow through the virus filter with constant or variable pressure during the filtration process.

Those of ordinary skill in the art will appreciate that the choice of filter type and mode (dead end filtration or tangential flow filtration) will depend on factors such as composition, the protein content, the molecular weight distribution, impurity/particulate load or any other biochemical or physical property in the feed to be processed, process requirements and limitations (allowable pressure, process time, volumes to be filtered) or characteristics of the potential viral contaminant, e.g. virus size. Availability of an in-process integrity test and logistics of viral clearance studies must also be taken into consideration. Dead end filtration should typically be employed for feed streams of high purity to yield a reasonable process flux whereas in some embodiments tangential flow filtration can accommodate feed streams with high particulate load. In some preferred embodiments normal flow filtration is preferred in combination with a continuous filtration mode using a least one virus filter having an effective pore size of maximum 75 nm. Of course, also this embodiment can be combined with all other parameters of the present invention.

Of course, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided might be different from the actual publication dates that may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Examples are provided below to illustrate the present invention. These examples are not meant to constrain the present invention to any particular application or theory of operation.

Example 1: Scale Down Virus Filtration with Different Virus Filters and Cell Culture Media Virus filtration membranes from different manufacturers (see Table 2) were assessed for their filtration kinetics in different filter sizes with cell culture media containing 4 g/L concentration of soy hydrolysates from different lots and suppliers (see Table 3). Cell culture media composition and preparation is described in Example 2. Filtration experiments were carried out either by controlling the pressure with a pressurized vessel (FIG. 3, FIG. 4, FIG. 5 and spiking experiments in FIG. 7, FIG. 8 and FIG. 9), or by controlling the flow rate e.g. by a peristaltic pump (FIG. 1, FIG. 2, FIG. 3 and FIG. 6). Other equipment used for temperature and pressure control of the experiments is described in Table 4.

TABLE 2

List of virus filters

| Internal filter code in Figures/Examples | Manufacturer/Product name/Size |
|---|---|
| Filter A | Sartorius Virosart CPV 180 $cm^2$ |
| Filter B | Millipore Viresolve NFP 3.1 $cm^2$ |
| Filter C | Pall Ultipor VF grade DV20 700 $cm^2$ |
| Filter D | Asahi BioEX 10 $cm^2$ |
| Filter E | Sartorius Virosart CPV 2000 $cm^2$ |
| Filter F | Millipore Viresolve NFP 850 $cm^2$ |
| Filter G | Asahi 15 N 10 $cm^2$ |
| Filter H | Pall Ultipor VF grade DV20 9.6 $cm^2$ |
| Filter I | Sartorius Virosart CPV 5 $cm^2$ |

TABLE 3

List of soy hydrolysates

| Internal soy hydrolysate code in Figures/Examples | Manufacturer/Product name/Internal lot number |
|---|---|
| Soy hydrolysate 1 | Kerry HyPep 1510 #1 |
| Soy hydrolysate 2 | DOMO SE50 MAF UF #1 |
| Soy hydrolysate 3 | DOMO SE50 MAF UF #2 |
| Soy hydrolysate 4 | DOMO SE50 MAF UF #3 |
| Soy hydrolysate 5 | Kerry HyPep 1510 #2 |
| Soy hydrolysate 6 | DOMO SE50 MAF UF #4 |
| Soy hydrolysate 7 | DOMO SE50 MAF UF #5 |

TABLE 4

List of equipment

WM Marprene bore mm × wall mm 3.2 × 1.6 and 1.6 × 1.6 (Watson Marlow)
Peristaltic pumps Watson Marlow 101U/R (Watson Marlow)
Pressure Vessel Sartorius Model 17532 (Sartorius-Stedim)
Pressure Transducers: Pascal Ci CL1010 (Labom) and KrosFlo ACPM-499-03N (Spectrum Labs)
Balance Sartorius FBG64EDE-SOCE (Sartorius Stedim)
Water Bath Haake DC10 (Thermo Scientific)
Temperature sensor CEM IR-68 Flexible InfraRed Thermometer

Example 2: Cell Culture Media Preparation

A general description of the cell culture media composition is provided in Table 5 below, with the composition of the different soy hydrolysates listed in Table 3 above. The different batches of cell culture media were sterile filtered with a sterile grade filter, e.g. a Pall Fluorodyne® II DJL Membrane Filter Cartridge 0.1μ prior to the different virus filtrations described in the examples. Media preparations described here were used for all experiments described and shown in FIG. 1 to FIG. 11.

TABLE 5

Media composition

| Component | Concentration [g/kg] |
|---|---|
| DMEM/HAMS F12 | 11.76 |
| Ethanolamine | 0.00153 |
| Lutrol F68 | 0.25 |
| Soy hydrolysate | 4.0 |
| Trace element - stock solution | Max. 4 μg/L |
| L-Glutamine | 0.6 |
| NaHCO$_3$ | 2.0 |
| Purified water | Ad 1 kg |

Example 3: Filter Preparation

The virus filters were prepared according to product manuals of virus filter manufacturers. Unless filters were delivered and assembled sterile, filters were autoclaved at >121° C. for 20 minutes.

Example 4: Integrity Test

After usage, filters of appropriate size (Filters A, C, E and F of Table 2) were washed according to the respective manufacturer's recommendations. A Forward Flow Test was performed with Palltronic Flowstar XC (Pall, US) according to the manufacturer's specifications. All integrity tests performed after filtration experiments described herein complied with specified limits.

Example 5: Proportional Relationship Between Differential Pressure and Flux

To investigate the relationship between pressure differential and volumetric flow rate, cell culture medium was subjected to filtration using autoclaved virus filters at ambient temperature. Media was filled into a pressure vessel and the virus filters connected to the pressure vessel, which was then pressurized at different levels. The specific flow rate and differential pressures were measured with a balance and a pressure transducer and recorded over time (FIG. 3).

Example 6: 10 L Scale-Down Fermentation System Model

A comparison of cell culture media with and without virus filtration was performed using a recombinant protein expressing CHO cell fermentation system (FIG. 6). The performance with regard to growth rate and yields was investigated. Cell culture medium as described in Example 2 was prepared. One part of the experiment was carried out with only sterile filtered medium, whereas the other part was carried out with the same medium and an additional virus filtration using a Sartorius Virosart CPV 180 cm$^2$. Filtration was carried out at 2-8° C. The fermentation experiment was carried out in Rushton type agitated 10 L benchtop bioreactors with inline controlled pH, pO2 and temperature. The parameter setpoints and ranges for the fermentation were as follows:

pH: 7.05 (6.8-7.3)
T: 37.0° C. (35-39° C.)
DO: 20% (Air saturation) (10-60%)

Cells were cultivated in batch mode followed by a chemostat culture using the media with and without additional virus filtration. Data from the chemostat mode (growth rates and productivity) were generated from a 4 week continuous cell culture.

Cell counts were determined by CASY measurement. In chemostat culture the specific growth rate (μ) was calculated by:

$$\mu = D + \ln(X_{t1}/X_{t0})/(t_1-t_0)$$

where D is the dilution rate calculated as ratio of medium feed rate per day and working volume [1/d]. Growth rates were calculated from CASY homogenized cell counts.

For biochemical analysis, the homogenous suspension was centrifuged with 400×g in a Heraeus Multifuge 1 S-R for 10 min and 1.0 mL aliquots were prepared in Eppendorf tubes and stored at ≤−20° C. Cell free supernatants were analyzed for the activity of an expressed recombinant protein by a chromogenic assay according to standard operating procedures.

The volumetric productivity P in this experiment was calculated by:

$$P[U/(L \times d)] = \text{Activity [mU/mL]} * \text{dilution rate } [d^{-1}]$$

The cell-specific productivity qP was calculated by:

$$qP[mU/(10E06 \text{ cells} \times d)] = P[U/(L \times d)]/\text{cell count } [10E06 \text{ cells/mL}]$$

Example 7: 120 L Scale-Down Fermentation System Model

A continuous virus filtration technique performed on a 120 L working volume of media prior to its addition to a recombinant protein expressing CHO cell fermentation system was investigated with regard to its effect on growth rate and yields (FIG. 6A, FIG. 6B and FIG. 6C). The study compared production processes using three variations of the same cell culture media: a) standard media; b) standard media filtered using Virosart CPV virus filters; and c) standard media filtered using Millipore Viresolve NFP virus filters.

During the continuous production process, the two different virus filters (Virosart CPV Midicap size 2000 cm$^2$ and Millipore Viresolve NFP size 850 cm$^2$) were used alternatively for different time intervals. The Sartorius CPV filter was used from culture day K00-K14, K23-K30 and K39-K63 and the Millipore NFP filter was used from culture day K14-K23 and K30-K39.

The parameter setpoints and ranges for the fermentation were as follows:
pH: 7.05 (6.8-7.3)
T: 37.0° C. (35-39° C.)
DO: 20% (Air saturation) (10-60%)
Sampling and Analysis Cell counts were determined by CASY® cell count and analyzer system. For biochemical analysis the homogenous suspension was centrifuged with 400×g in a Heraeus Multifuge 1 S-R (Thermo Scientific, USA) for 10 min. Cell free supernatants were analyzed for the activity of an expressed recombinant protein by a chromogenic assay.

In chemostat culture the specific growth rate (μ) was calculated by:

$$\mu = D + \ln(X_{t1}/X_{t0})/(t_1-t_0)$$

where D is the dilution rate calculated as ratio of medium feed rate per day and working volume [1/d]. Growth rates are calculated from CASY homogenized cell counts.

The volumetric productivity P in this experiment was calculated by:

$$P[U/(L*d)] = \text{Activity } [mU/mL] * \text{dilution rate } [d-1]$$

The cell-specific productivity qP was calculated by:

$$qP[mU/(10E06 \text{ cells} \times d)] = P[U/(L*d)]/\text{cell count } [10E06 \text{ cells/mL}]$$

Example 8: Virusfiltration with ASAHI Planova 15N Virus Filters

Soy hydrolysate containing media (DOMO SE50 MAF #5) were spiked with MMV and placed into a tank connected to a pressurized nitrogen gas supply. The MMV-spiked material was passed through a 10 cm$^2$ ASAHI Planova 15N virus filter set-up in-line in a dead-end mode at a constant pressure of 1100 mbar (set-point). The minimum and maximum values of following parameters were measured and recorded continuously: Feed pressure; feed, filtrate and ambient temperature and filtrate weight (the change of which was used to calculate the filtrate flow rate). Samples were taken daily for up to 7 days and analyzed for MMV virus titer (FIG. 7).

Example 9: Virusfiltration with ASAHI Planova BioEX Virus Filters

Soy hydrolysate containing media (Run #1 with soy hydrolysate DMV SE50 MAF UF #5); Run #2 with soy hydrolysate SDMV SE50 MAF UF #4) were spiked with MMV and placed into a tank connected to a pressurized nitrogen gas supply. The MMV-spiked material was passed through a 10 cm$^2$ ASAHI Planova BioEX virus filter set-up in-line in a dead-end mode at a constant pressure of 2000 mbar (set-point). The minimum and maximum values of following parameters were measured and recorded continuously: Feed pressure; feed, filtrate and ambient temperature and filtrate weight (the change of which was used to calculate the filtrate flow rate). Samples were taken daily for 5 days and analyzed for MMV virus titer (FIG. 8).

Example 10: Virusfiltration Summary

Cell culture media containing different soy hydrolysates were spiked with MMV and placed into a tank connected to a pressurized nitrogen gas supply. Different virus filters were used in combination with the different soy hydrolysates as listed in Table 6:

TABLE 6

Combination of virus filters and soy hydrolysates used in spiking experiments

| Experiment # | Filter | Soy hydrolysate Lot | Run time [days] |
|---|---|---|---|
| 1 | D | 7 | 5 |
| 2 | D | 6 | 5 |
| 3 | I | 3 | 19 |
| 4 | I | 5 | 17 |
| 5 | G | 7 | 7 |
| 6 | G | 7 | 6 |
| 7 | B | 6 | 14 |
| 8 | H | 3 | 11 |

Filtrations were set-up in a dead-end mode at a constant pressure of 2 bar (set-point) for all runs except for the runs Experiments #5 and 6 which were performed at a constant pressure of 1.1 bar (set-point). The minimum and maximum values of following parameters were measured and recorded continuously: Feed pressure; feed, filtrate and ambient temperature and filtrate weight (the change of which was used to calculate the filtrate flow rate). Samples were taken during the run time of the experiment and analyzed for MMV virus titer. Overall log reductions were calculated from the difference of the total virus infectivity load in the filtrate and the total virus infectivity load prior to filtration (FIG. 9).

Example 11: Long Term Filtration with MMV Virus Spike

Cell culture medium as described in Example 2 was spiked with MMV to a titer of $5.0[\log_{10}(TCID_{50}/mL)]$ and subjected to a long term filtration of 30 days over a 20 nm pore-size viral filter (Sartorius Visrosart CPV 5 cm$^2$). Filtration was carried out with a set-up comparable to Example 9 and Example 10, but with constant pressure of 1.1 bar (specified range: 0.8 bar to 1.2 bar) and with regular pressure and flow interruptions to challenge the viral filter. Flow rates in the course of the experiment were recorded and maintained above 4 L/(m$^2$×hr) (FIG. 10).

20 samples of the filtrate were taken (up to 5 times per week) and the MMV virus titer and load determined. No virus break-through was observed in any of the 20 fractions assayed. Virus loads ranged from $<0.9[\log_{10}(TCID_{50})]$ to $<2.8[\log_{10}(TCID_{50})]$ depending on fraction volume. The total virus load in the filtrates was $<3.0[\log_{10}(TCID_{50})]$ which—when subtracted from the initial virus load of the spiked material (i.e. $8.5[\log_{10}(TCID_{50})]$)—results in an overall virus reduction factor of $>5.5 \log_{10}$. This was seen to be effective and complete (FIG. 11).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. A method for removing a viral contaminant from a preparation, said preparation being a cell culture medium or at least one component of a cell culture medium, comprising the step of:
   a) subjecting said preparation to filtration for at least about 24 hours through a virus filter having an effective pore size of maximum 75 nm, wherein the same virus filter is used for at least 24 hours and the filtration operates at a volumetric capacity of at least about 2000 L/m$^2$.

2. The method of claim 1, wherein said preparation is subjected to filtration for at least about 48 hours to about 7 months.

3. The method of claim 1, further comprising the step:
   b) feeding the filtrate to a cell culture medium or to at least one component of a cell culture medium.

4. The method of claim 1, wherein the filtration is a continuous filtration.

5. The method of claim 1, wherein the filtration is performed at a temperature from about 2° C. to about 60° C.

6. The method of claim 1, wherein said virus filter achieves at least a 1 Log 10 reduction value (LRV) for a viral contaminant.

7. The method of claim 1 where the filtration is performed using two or more filters arranged in series, in parallel, or a mixture of both.

8. The method of claim 7, wherein the filtration is performed using two filters arranged in parallel in a system of tubes comprising a Y-shaped junction and wherein each filter is in fluid communication with a branch of the Y-shaped junction and a preparation supply source.

9. The method of claim 1, wherein the filtration is performed at a pressure ranging from about 100 mbar to about 4000 mbar.

10. The method of claim 1, wherein said virus filter is autoclavable.

11. The method of claim 1, wherein the cell culture medium comprises soy hydrolysate.

12. The method of claim 1, wherein the filtration operates at a volumetric capacity of at least about 5000 L/m$^2$.

13. The method of claim 2, wherein said preparation is subjected to filtration for at least about 72 hours to about 3 months.

14. The method of claim 5, wherein the filtration is performed at a temperature from about 15° C. to about 37° C.

15. The method of claim 9, wherein the filtration is performed at a pressure ranging from about 1000 mbar to about 3000 mbar.

16. The method of claim 1, wherein said preparation is subjected to filtration for at least about 48 hours to about 7 months.

17. The method of claim 4, wherein said preparation is subjected to filtration for at least about 48 hours to about 7 months.

18. The method of claim 5, wherein said preparation is subjected to filtration for at least about 48 hours to about 7 months.

19. The method of claim 9, wherein said preparation is subjected to filtration for at least about 48 hours to about 7 months.

* * * * *